(12) United States Patent
Hagler

(10) Patent No.: US 6,999,165 B2
(45) Date of Patent: Feb. 14, 2006

(54) METHOD AND APPARATUS FOR RADIATION ANALYSIS AND ENCODER

(75) Inventor: Thomas W. Hagler, Grass Valley, CA (US)

(73) Assignee: Aspectrics, Inc., Pleasanton, CA (US)

( * ) Notice: Subject to any disclaimer, the term of this patent is extended or adjusted under 35 U.S.C. 154(b) by 0 days.

(21) Appl. No.: 09/848,614

(22) Filed: May 3, 2001

(65) Prior Publication Data

US 2004/0174522 A1 Sep. 9, 2004

Related U.S. Application Data

(63) Continuation-in-part of application No. PCT/US99/14446, filed on Jun. 25, 1999, and a continuation of application No. 09/105,279, filed on Jun. 26, 1998, now Pat. No. 6,271,917.
(60) Provisional application No. 60/202,371, filed on May 4, 2000.

(51) Int. Cl.
*G01J 3/04* (2006.01)
*G02B 26/02* (2006.01)

(52) U.S. Cl. ...................................... 356/310; 359/236
(58) Field of Classification Search ................. 356/310; 250/226; 259/236
See application file for complete search history.

(56) References Cited

U.S. PATENT DOCUMENTS 3,563,654 A   2/1971  Vermande ................... 356/330
3,578,980 A   5/1971  Decker et al. ............ 250/237 G
3,586,442 A   6/1971  Tripp ........................... 62/107
3,639,062 A   2/1972  Girard et al. ................ 356/330

(Continued)

FOREIGN PATENT DOCUMENTS

| GB | 672758 A | 5/1952 |
| WO | WO97/31245 | 8/1997 |

OTHER PUBLICATIONS

"Static Multislit Spectrometry and Its Application to the Panoramic Display of Infrared Spectra," Marcel J.E. Golay, *Journal of the Optical Society of America*, vol. 41, No. 7, Jul. 1951, pp. 468–472.

"Multi–Slit Spectrometry," Marcel J.E. Golay, *Journal of the Optical Society of America*, vol. 39, No. 6, Jun. 1949, pp. 437–444.

A Multiplex Grating Spectrometer, J.F. Grainger t al., *Journal de Physique*, Colloque C2, supplément au n° 3–4,Tome 28, Mars–Avril 1967, pp. C2–44—C2–52.

Search Report mailed Oct. 21, 1999, issued for parent U.S. Appl. No. 09/105,279, filed Jun. 26, 1998, now U.S. Pat. No. 6,271,917.

International Search Report mailed Jan. 11, 2000, issued for parent U.S. Appl. No. 09/105,279, filed Jun. 26, 1998, now U.S. Pat. No. 6,271,917.

*Primary Examiner*—Zandra V. Smith
(74) *Attorney, Agent, or Firm*—Fenwick & West LLP

(57) ABSTRACT

Method and apparatus for analyzing radiation using analyzers and encoders employing the spatial modulation of radiation dispersed by wavelength or imaged along a line.

13 Claims, 19 Drawing Sheets

U.S. PATENT DOCUMENTS

| | | | |
|---|---|---|---|
| 3,640,625 A | 2/1972 | Ibbett et al. | 356/310 |
| 3,922,092 A | 11/1975 | van den Bosch | 350/332 |
| 4,007,989 A | 2/1977 | Wajda | 356/310 |
| 4,264,205 A | 4/1981 | Landa | 356/326 |
| 4,304,491 A | 12/1981 | Kraushaar et al. | 356/326 |
| 4,448,529 A | 5/1984 | Krause | 356/310 |
| 4,450,459 A | 5/1984 | Turner et al. | 347/239 |
| 5,024,508 A | 6/1991 | Horner | 359/561 |
| 5,090,807 A | 2/1992 | Tai | 356/310 |
| 5,121,239 A | 6/1992 | Post | 359/271 |
| 5,235,461 A | 8/1993 | Kirsch et al. | 359/561 |
| 5,325,324 A | 6/1994 | Rentzepis et al. | 365/127 |
| 5,483,335 A | 1/1996 | Tobias | 356/310 |
| 5,485,268 A | 1/1996 | Tobias | 356/310 |
| 5,504,575 A | 4/1996 | Stafford | 356/330 |
| 5,537,303 A | 7/1996 | Stacy | 362/284 |
| 5,579,105 A | 11/1996 | Belton et al. | 356/310 |
| 5,592,327 A | 1/1997 | Gabl et al. | 359/348 |
| 5,691,886 A | 11/1997 | Stacy | 362/283 |
| 5,748,308 A | 5/1998 | Lindberg et al. | 356/310 |
| 5,991,460 A | 11/1999 | Mitchell | 382/278 |
| 6,011,640 A | 1/2000 | Hutton | 359/234 |
| 6,018,402 A | 1/2000 | Campbell et al. | 359/22 |
| 6,101,034 A | 8/2000 | Cox et al. | 359/562 |
| 6,271,917 B1 | 8/2001 | Hagler | 356/310 |
| 6,388,794 B2 * | 5/2002 | Hagler | 250/226 |

\* cited by examiner

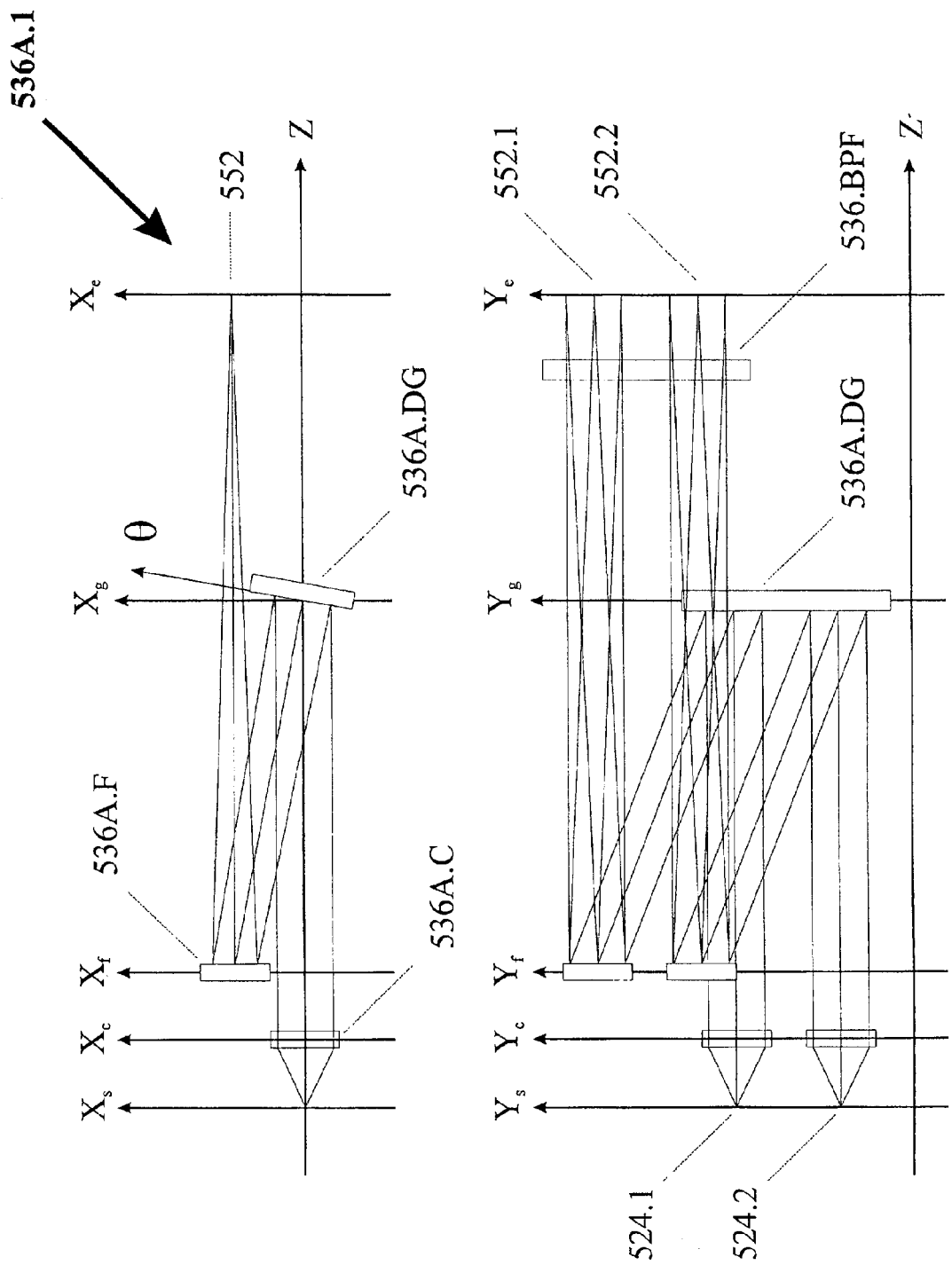

METHOD AND APPARATUS FOR RADIATION ANALYSIS AND ENCODER

CROSS REFERENCE TO RELATED APPLICATION

This application is a continuation-in-part of co-pending U.S. patent application Ser. No. 09/105,279, filed Jun. 26, 1998 now U.S. Pat. No. 6,271,917, International Application Ser. No. PCT/US99/14446, filed Jun. 25, 1999, and of U.S. Provisional Application Ser. No. 60/202,371, filed May 4, 2000.

BACKGROUND OF THE INVENTION

This invention relates in general to radiation spectrum analyzers and radiation image analyzers, and in particular, to radiation analyzers and encoders employing the spatial modulation of radiation dispersed by wavelength or imaged along a line.

Radiation spectral analysis is presently carried out in a number of ways. Dispersive and Fourier transform based analyzers are for high resolution and can be used for many different applications so that they are more versatile than existing application-specific instruments and procedures. While these analyzers offer superior spectral performance, they tend to be expensive, large, heavy and non portable. For most applications, these instruments offer a resolution which is largely unnecessary. Many applications require measurements only at several wavelengths so that most of the data taken over the entire complete spectrum using these instruments is discarded and not used in the analytical computations. The processing of the additional, unnecessary data reduces the speed of these instruments.

In contrast, a non-dispersive approach to spectral analysis employs a radiation source filtered by one or more bandpass to provide input to a specific analytical function. The bandpass filters are used to select one or more specific spectral components which are characterized by a center wavelength and bandwidth. One of the principal advantages of the non-dispersive approach is the ability to individually specify the center wavelength and bandwidth of the bandpass filters to optimize the instrument for a particular application. However, if the analytical function requires a significant number of filters, the system's signal-to-noise ratio is reduced as the total energy measured in a given filter over time is inversely related to the number of filters. Furthermore, if a spectrum analyzer using this approach is configured for a first application, the filters used in the device may have to be replaced, or the number of filters changed, in order to adapt the analyzer to a second application. As a consequence, the non-dispersive approach has clear limitation in adaptability and the number of spectral components which can be analyzed.

Another type of optical spectrum analyzer, which is best described as a hybrid between dispersive and non-dispersive instruments, is the Hadamard spectrometer. The Hadamard spectrometer includes a spatial radiation modulator, comprised of a disc made of an opaque material with slots therein that reflect or transmit radiation, where the slots have uniform transmittance or reflectance. A radiation beam is dispersed according to wavelength onto the disc and the slots are selectively spaced at different radii from the axis to form a number of different optical channels for detecting corresponding spectral components of the beam. The disc is rotated about the axis and the slots selectively encode the corresponding spectral components with a binary amplitude modulation. The encoded beam is then directed to a detector.

In order to differentiate the intensity of the spectral component transmitted or reflected by one slot from that of another, the disc is sequentially stepped through a specific number of steps, each step comprised of a binary pattern of open or closed optical channels, which defines one equation in a system of simultaneous equations for the amplitudes of the spectral components. This set of simultaneous equations is then solved to yield the intensity for each channel prior to any specific analytical function, an approach which is time consuming and prone to errors. Furthermore, as a direct consequence of the binary encoding approach, there is no mechanism by which one can recover the actual signal levels if any one of the signal levels changes substantially over the period of rotation. It should be noted that the system of equation can be simplified if the slots are patterned such that the radiation is transmitted or blocked one spectral component at a time. However, this approach changes the optical duty cycle of each of the spectral components from its optimum value of 50%, thereby degrading the signal to noise ratio. Finally, if a Hadamard analyzer is configured for a first application, and the number of slots is changed to adapt the analyzer to a second application, the data acquisition and decoding algorithms must be changed as well, which significantly limits the instrument's adaptability.

Radiation imaging is primarily carried out using detector arrays and Charge Couple Devices (CCDs). Much of the data analysis required by these techniques results from the mapping of the image onto a regular array of detector elements. A significant reduction in the required data analysis would be realized if the detector array elements could be configured for the specific image measured in the application. Infrared detector arrays are susceptible to background radiation, inter-detector-element drift and 1/f noise. Imaging systems based on infrared detector arrays typically require a large Thermo-Electric (TE) cooler and are very expensive. Because of their modest sensitivity, CCD-based imaging systems typically require a TE cooler and long exposure times in low light level application such as fluorescence imaging. A significant performance advantage could be realized in fluorescence imaging if the pixels of the CCD camera could be replaced with individual, inter-calibrated Photo-Multiplier Tubes (PMTs). Unfortunately, a low-cost, high-density detector array based on a PMT simply does not exist.

None of the above approaches is entirely satisfactory. It is, therefore, desirable to provide improved spectrum and image analyzers where the above-noted disadvantages are avoided or significantly diminished, and where the encoding, data acquisition and decoding are both generalized and significantly simplified such that the details of the spectrum or image analyzer can be rendered to a single application specific hardware component.

SUMMARY OF THE INVENTION

This invention provides many advantages over the radiation analyzers described above in that the intensity of the incident radiation is modulated independent of the bandwidth and that the amplitude of the modulated signal is a smooth function or changes between three or more distinct levels of contrast as the modulator is rotated about an axis or otherwise reciprocated. Using the present invention, one can implement a multi-channel orthogonal encoding scheme for arbitrary center wavelengths and bandwidths and arbitrary radial intensity distributions. In this manner, the center wavelengths and bandwidths of the encoded channels can be independently optimized for a specific application. The present invention combines the before mentioned optical encoding scheme with imaging optics so that radiation from an extended source or collection of discrete samples can be imaged using a single detector. The present invention allows one to control the modulation depth on a channel-by-channel basis independent of the bandwidth, a design strategy which may be useful for balancing signal levels in systems where one or more channels have a disproportionately large fraction of the total incident radiation. The present invention allows one to group modulation channels into complementary pairs where the amplitude and phase of the resulting encoded component is determined by the relative portion of radiation incident on the two filters comprising the pair. In this manner, intensity differences, wavelength derivatives, and the radial position of the center of an intensity distribution can be measured directly. The present invention allows one to use one or more complementary filter pairs in conjunction with an expected radiation component for calibration and alignment purposes. The present invention allows one to use a dedicated light source and detector and a series of marks on the modulator to detect spindle wobble, vibrations or a misaligned modulator pattern on the modulator substrate for calibration and alignment purposes. The present invention allows one to measure a plurality of response radiation components as a function of two or more excitation components substantially simultaneously, enabling a fast, compact fluorescence, Raman or photorefractive excitation/response analyzer. The present invention allows one to use modulation functions which are based on incomplete periods of the rotation of the modulator, which can be used to eliminate various hardware items, free up micro-processor resources, synchronize the movements of external mechanical devices, measure both the radial position and the intensity of an imaged radiation component, and increase the spatial or spectral resolution of the analyzer. Finally, the present invention allows one to measure a plurality of spectral components individually selected from a collection of radiation emitting samples substantially simultaneously using a one-dimensional hyper-spectral imaging optic and a single channel detector.

In one embodiment of the invention, a spectrum analyzer is comprised of at least one source providing radiation having at least one selected spectral component, the spectral component having an intensity, a center wavelength and a bandwidth. A first optic is used to collect, disperse and focus the radiation to form an image dispersed by wavelength along an encoding axis onto an encoding plane. A two-dimensional spatial radiation modulator is rotated about a rotation axis and positioned in the encoding plane so that the encoding axis is substantially along a radial axis of the modulator. The modulator has at least one radiation filter at a radius from the rotation axis having a radial width substantially defining the bandwidth of a corresponding spectral component of the radiation. The filter modulates the intensity of the corresponding spectral component substantially independent of the bandwidth to provide an encoded beam comprised of at least one encoded component, wherein the amplitude of the encoded component is a smooth function or changes between three or more substantially distinct levels of contrast as the modulator is rotated about the rotation axis. Preferably, at least two of the filters have substantially orthogonal modulation functions along an azimuthal axis. Most preferably, at least one of the filters modulates the intensity of a spectral component substantially according to a digitized replica (e.g., a halftone representation) of a function of the form $\sin^2(m\theta+p\pi/4)$, where $\theta$ is the rotation angle of the modulator about the axis and m is an integer. A second optic is used to collect and direct the encoded beam onto a detector, and a computer is used to analyze the signals generated by the detector in response to the encoded beam. Preferably, the computer uses a decoding algorithm to compute the amplitude of at least one encoded component from the signals generated by the detector in response to the encoded beam. If radiation in two or more spectral ranges is to be analyzed simultaneously, a number of dichroic mirrors can be used to focus two or more dispersed images onto the modulator and two or more detectors can be used to detect the radiation.

In another embodiment of the invention, an image analyzer for analyzing the radiation from an extended source having at least two spatial components that emit, transmit or reflect radiation is comprised of a first optic collecting and focusing radiation from the extended source to form at least two corresponding images along an encoding axis onto an encoding plane. One example of an extended source is a collection of different samples which emit, scatter, transmit or reflect radiation. In this case the individual samples are imaged along an encoding axis onto an encoding plane, such that each sample is focused at a substantially different point along the encoding axis. Another example of an extended source is one or more radiation sources which is filtered by two or more bandpass filters. In this case the radiation transmitted through (or, alternatively, reflected from) the collection of bandpass filters is imaged along an encoding axis onto an encoding plane, such that the radiation filtered by each bandpass filter is focused at a substantially different point along the encoding axis. A two-dimensional spatial radiation modulator is rotated about a rotation axis and positioned in the encoding plane so that the encoding axis is along a radial axis. The modulator has at least one radiation filter at a radius from the rotation axis for modulating the intensity of a corresponding spatial component to provide an encoded beam comprised of at least one encoded component. Preferably, the amplitude of the encoded component is a smooth function or changes between three or more substantially distinct levels of contrast as the modulator is rotated about the rotation axis. Most preferably, at least one of the filters modulates the intensity of a spectral component substantially according to a digitized replica (e.g., a halftone representation) of a function of the form $\sin^2(m\theta+p\pi/4)$, where $\theta$ is the rotation angle of the modulator about the axis and m is an integer. A second optic is used to collect and direct the encoded beam onto a detector, and a computer is used to analyze the signals generated by the detector in response to the encoded beam. Preferably, the computer uses a decoding algorithm to compute the amplitude of at least one encoded component from the signals generated by the detector in response to the encoded beam. If radiation from two or more extended sources of radiation are to be analyzed simultaneously, the images from the extended sources can be focused onto different surfaces or different radial axes of the modulator and two or more detectors can be used to detect the radiation. In the preferred embodiment of the image analyzer, the extended source will contain a number of reference spatial components and the modulator will contain a number of dedicated filters to provide feedback for the alignment of the image onto the modulator pattern. For some applications, it may be desirable to further analyze the spatially encoded radiation from the extend source for one or more spectral properties. This may be performed by inserting a spectrum analyzer or other wavelength filtering device between the modulator and the detector.

In the preferred embodiment of the spectrum and imaging analyzers described above, the two-dimensional spatial radiation modulator contains a series of timing marks and the analyzer has a number of optical switches which are triggered by the timing marks to establish the absolute angle of rotation for decoding purposes. Most preferably, the timing marks will also trigger the data acquisition (DAQ) from the detector and the decoding algorithm, which in turn, will substantially relax the requirements on the stability of the modulators rotational period. Preferably, the analyzer will have a dedicated radiation source and an analog detector which is partially interrupted by the timing marks and/or other marks located on the modulator or spindle to detect spindle wobble or a misaligned pattern on the modulator. More preferably, the signal generated by the analog detector are processed by the computer to provide the decoding algorithm and/or the analytical function with one or more calibration coefficients used to compensate for the undesired effects of spindle wobble or a misaligned pattern. Most preferably, the signal generated by the analog detector are processed by the computer to provide a control signal to position of one or more optical elements to keep the image or dispersed image centered on the modulator pattern.

In the preferred embodiment of the spectrum and imaging analyzers described above, the analyzers computer will include a transient-signal algorithm which will detect transients in the amplitudes of the encoded components which occur during a rotational period of the modulator. Preferably, the computer will analyze the transient signal to determine its harmonic content. More preferably, the harmonic content will be used by the decoding algorithm to compensate for transient-induced harmonic interference. Preferably, the transient-signal algorithm will include a feedback mechanism to increase the motor speed in response to the detection of sub-rotational-period signal transients and decrease the motor speed in response to extended periods of time where the amplitudes are stable.

Another aspect of the invention and useful for the above-described spectrum and image analyzers is a spatial radiation modulator adapted to be rotated about a rotation axis to modulate at least one component of an incident radiation beam to provide an encoded beam. The modulator is comprised of a substrate and at least one radiation filter located at a radius from the rotation axis. The filter is comprised of an annular region substantially encompassing a plurality of pixels having optical characteristics substantially different from the substrate. The pixels are patterned substantially within the annular region to modulate the intensity of a corresponding radiation component predominantly along an azimuthal axis to provide an encoded component such that the amplitude of the encoded component changes between three or more substantially distinct levels of contrast as the substrate is rotated about the rotation axis. Preferably, the density of the pixels is used to control the modulation depth of the encoded component. In this manner, the amplitudes of two or more encoded components can be balanced when one of the components has a disproportionate fraction of the total incident radiation.

Another aspect of the invention and useful for the above-described spectrum and image analyzers is a two-dimensional radiation modulator adapted to be rotated about a rotation axis to modulate at least one component of an incident radiation beam to provide an encoded beam. The modulator is comprised a substrate and at least one radiation filter located at a radius from the rotation axis. The filter has substantially continuously variable optical characteristics along an azimuthal axis, and the optical characteristics are continuously varied to modulate the intensity of a corresponding radiation component as a substantially smooth function of a rotation angle of the modulator about the rotation axis.

Another aspect of the invention and useful for the above-described spectrum and image analyzers is a two dimensional spatial radiation modulator adapted to be rotated about a rotation axis, or otherwise reciprocated in a direction. The modulator includes at least one radiation filter pair for modulating the intensity of an incident radiation beam to provide an encoded beam comprised of at least one encoded component. The pair is comprised of two radiation filters located at different radii from the rotation axis and having modulation functions that are complementary to each other so that the amplitude and phase of the resulting encoded component is determined by the relative proportion of radiation incident on the two filters. In that manner, the difference in the radiation intensity incident on the two filters can be measured directly rather than inferring the difference by subtraction, an inefficient approach which is prone to errors and which wastes the dynamic range of the detector signal. Preferably, the modulation functions are smooth functions or digitized replicas of smooth functions having three or more distinct levels of contrast. More preferably, the modulation functions of two filter pairs for modulating two different radiation component differences are substantially orthogonal to one another.

Another aspect of the invention and useful for the above-described spectrum and image analyzers is a two dimensional spatial radiation modulator adapted to be rotated about a rotation axis, or otherwise reciprocated in a direction. The modulator includes at least one radiation filter pair for measuring the difference in the radiation intensity incident on the two filters comprising the pair and a third radiation filter for measuring the sum of the radiation intensity incident on the two filters. In this manner, both the radial position of the center of the intensity distribution and the total intensity can be measured substantially simultaneously.

In some applications, it may be desirable to measure a samples response to two or more different excitation components substantially simultaneously. For example, some samples are altered by the excitation radiation such that the results of the measurements may differ depending upon which excitation component is first used in a series of measurements employing different excitation components. Another example where it may be desirable to measure a samples response to two or more different excitation components substantially simultaneously is a sample which is flowing in a process stream where the dwell time of the sample at the location of the measurement is insufficient to make the excitation measurements in sequence. In another embodiment of the invention, one or more excitation sources provides excitation radiation comprised of two or more distinct excitation components. For example, a diffractive or refractive optic may be used to spatially separate the spectral lines of a multi-line laser. The excitation components (e.g., the spectral lines) are directed to the sample substantially in sequence. In response to excitation radiation, the sample emits a response beam of radiation comprised of at least one response component emitted, transmitted, reflected or scattered in response to the excitation radiation. The response beam of radiation is collected and an image or a dispersed image is formed along an encoding axis in an encoding plane. A two-dimensional spatial radiation modulator rotated about a rotation axis and positioned in the encoding plane so that the encoding axis is along a radial axis. The modulator has at least one radiation filter at a radius from the rotation axis. The radiation filter modulates the intensity of a corresponding response component to provide an encoded response beam comprised of at least one encoded response component. Preferably, the modulation functions of the modulator which encode the response components are smooth functions or are digitized replicas of smooth functions having three or more distinct levels of contrast. The encoded response beam is collected and directed to a detector and the resulting signal is analyzed by a computer to computes the amplitude of at least one encoded response component as a function of the two or more excitation components. Preferably, the modulator used to encoded the response components is also used for directing the components of excitation radiation to the sample substantially in sequence. Preferably, the excitation sequence is synchronized with the data acquisition of the encoded response beam so that the response components corresponding to one excitation component may be distinguished from those corresponding to other excitation components. More preferably, the time-based detector signal is sorted into sub-signals, where each sub-signal corresponds to the encoded response components corresponding to only one of the excitation components.

In another embodiment of the invention, an analyzer for monitoring radiation from at least one radiation source comprises an input beam comprised of at least one radiation component corresponding to a distinct radiation source and having an intensity and a center wavelength. The input beam is collected and dispersed to form at least one image along an encoding axis onto an encoding plane, where the image corresponds to the component. A two-dimensional spatial radiation modulator rotated about a rotation axis and positioned in the encoding plane so that the encoding axis is substantially along a radial axis such that a change in the center wavelength of the component will cause the corresponding image to move substantially along the radial axis. The modulator has at least one radiation filter pair for modulating the intensity of a corresponding component to provide an encoded beam comprised of at least one encoded component. The filter pair is comprised of two radiation filters located at different radii from the rotation axis and having modulation functions that are complementary or out of phase so that the amplitude and phase of the encoded component is determined by the relative proportion of radiation incident on the two filters. Preferably, the radiation filters comprising the pair are substantially adjacent to one another. More preferably, the border between the adjacent radiation filters is substantially located at the radius which correspond to the nominal or desired center wavelength for the radiation source. The encoded beam is collected and directed to a detector and a computer analyzes the signals generated by the detector in response to the encoded beam. Preferably, the computer computes the amplitudes and phases of at least one encoded component from the signals generated by the detector in response to the encoded beam. More preferably, the computer generates at least one control signal for adjusting the center wavelength of at least one source in response to the signals generated by the detector to tune the source. Preferably, at least two of the encoded components are encoded with substantially orthogonal modulation functions, and computer computes the amplitude and phase of at least one of the encoded component. Preferably, each of the modulation functions is a smooth function or a digitized replica of a smooth function having three or more distinct levels of contrast. Preferably, the analyzer will have one or more optical elements on movable stages such that the images can be collectively displaced along the radial axis of the modulator. In this manner, the instrument can be calibrated, and periodically, the source images can be purposely offset with respect to the filter pairs on the modulator in order to measure the intensity of the radiation sources. More preferably, the modulator can be segregated into two halves, the first half containing complementary pairs for monitoring the wavelength and the second half containing individual filters to measure the intensity. In this manner, the analyzer can provide a control signal to stabilize the sources wavelength and measure the sources intensity. By adding addition filter pairs which are orthogonal to other filter pairs, more than one radiation source may be monitored at the same time.

BRIEF DESCRIPTION OF THE DRAWINGS

FIG. 12A is a schematic of one embodiment of a one-dimensional hyper-spectral pre-encoder optic.

DETAILED DESCRIPTION OF THE PREFERRED EMBODIMENT

Figure 1:
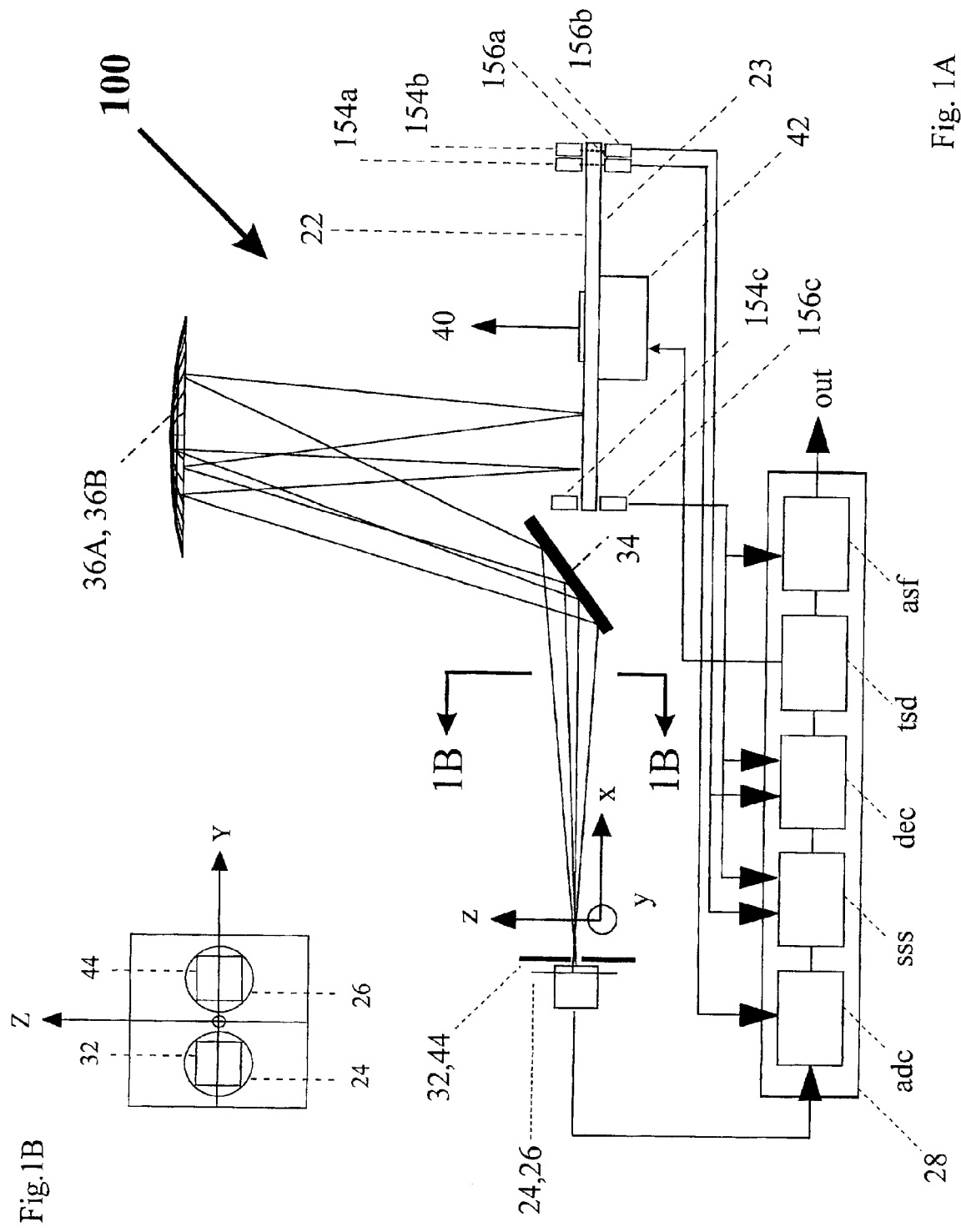
FIG. 1A is a schematic side view of the dual-use radiation analyzer to illustrate the preferred embodiment of the invention.
FIG. 1B is a schematic view illustrating a view along the line 1B—1B in FIG. 1A of a portion of the analyzer in FIG. 1A.

Because of the dual use of the present invention as a spectrum analyzer and as an image analyzer it is convenient to generalize certain terms and phrases used in the descriptions that follow. In the descriptions of the present invention that follow we shall use the following dual-use notation for brevity:

1. RADIATION SOURCE: radiation sources having spectral components, radiation sources having spatial components, or radiation sources having both spectral and spatial components. The radiation source can be a sample or collection of samples which emit, scatter, transmit or reflect radiation in response to one or more components of excitation radiation.

2. RADIATION COMPONENTS: portions of the radiation from the radiation source having spectral information, portions of the radiation from the radiation source having spatial information, or portions of the radiation from the radiation source having both spectral and spatial information.

3. PRE-ENCODER OPTICS: one or more optical elements which form one or more images, or one or more dispersed images on a surface of the modulator. The pre-encoder optic may include one or more optical fibers, wave guides, or light pipes, for coupling radiation from one or more remote sources to the analyzer.

4. POST-ENCODER OPTICS: one or more optical elements which collect the encoded radiation from the modulator and direct and focus the encoded beam onto one or more radiation detectors. The post-encoder optic may include one or more optical fibers, wave guides, or light pipes, for coupling encoded radiation from the instrument to one or more remote sampling stations.

5. TARGET IMAGE: an image comprised of two or more radiation components substantially separated from one another along an encoding axis. The width of the target image is the spatial extent perpendicular to the encoding axis.

6. IMAGING: collecting and focusing the source radiation to form one or more images, or collecting, dispersing and focusing the source radiation to form one or more dispersed images along a common axis.

7. ALIGNMENT COMPONENTS: anticipated or expected radiation components which are used in conjunction with complementary filter pairs to gauge the alignment of the target image onto the modulator pattern.

Dual-Use Radiation Anlyzer 100

FIG. 1A is a schematic view of dual-use radiation analyzer 100 (which can be configured as a spectrum analyzer, an image analyzer, or a hyper-spectral imaging analyzer), to illustrate a preferred embodiment of the invention where the encoding of the selected spectral or spatial components is achieved by spatially varying the reflectance properties of a rotating spatial radiation modulator. As shown in FIG. 1A, analyzer 100 includes a spatial radiation modulator 22, which is comprised of a pattern formed on a surface of modulator substrate 23, for encoding radiation from a source 24, which may be a broadband or multiple wavelength source containing spectral information, an extended source containing spatial information, or any combination thereof. An input radiation beam from source 24 is preferable passed through an entrance aperture 32 to a folding mirror 34 which reflects the radiation to pre-encoder optic 36A which images the input radiation to form target image 52 onto modulator 22 such that the radiation components of 52 are focused at substantially different points along a radial axis of modulator 22. If more than one target image is to be encoded substantially simultaneously, additional optical elements (not shown) can be used to focus two or more target images onto modulator 22 and collect and direct the encoded beams onto an equal or greater number of radiation detectors.

Modulator substrate 23 rotates on a motorized spindle 42 about a rotation axis 40 in the encoding plane. Preferably, modulator 22 contains a sub-pattern of timing and/or location marks which interrupt the optical switches described below for timing and alignment purposes. More preferably, this sub-pattern includes at least two series of marks confined to annular regions at different radii, one series having marks at regular angular intervals and the other series having marks at non-regular angular intervals. In this manner, the exact rotation angle of modulator can be established by computer 28 for decoding purposes. Modulator 22 has at least one radiation filter at a radius from rotation axis 40 which modulates (or encodes) the intensity of a corresponding radiation component to provide an encoded beam comprised of at least one encoded component, wherein the amplitude of the encoded component is a smooth function or changes between three or more substantially distinct levels of contrast as the modulator is rotated about rotation axis 40. For convenience in description, the spatial radiation filters on modulator 22 are described to reflect radiation, it being understood that spatial radiation filters that transmit instead of reflect radiation may be used instead in each of the embodiments herein and such variations are within the scope of the invention. The encoded radiation beam reflected by modulator 22 is collected, directed and focused by post-encoder optic 36B towards folding mirror 34 which reflects the beam towards an exit aperture 44 onto detector 26. Detector 26 detects the total intensity of the different encoded radiation components in the encoded beam to provide a detector output to computer 28.

The optical geometry illustrated in FIG. 1A was chosen for clarity, as it has the fewest number of optical components. Other optical geometries which involve separate, and more elaborate optical systems to collect and focus the input radiation onto modulator 22 and to collect and focus the encoded beam from modulator 22 onto detector 26 may be used instead in each of the embodiments herein and such variations are within the scope of the invention. For example, additional optical elements which render the dominant plane of incidence parallel to the plane of modulator 22 are useful for reducing the size of the instrument.

In another embodiment of the present invention, detector 26 can be replaced with an optical fiber bundle and a number of remote sampling stations which include a detector and a computer similar to computer 28 described below. In this manner, a number of remote measurements can be made substantially simultaneously by propagating the encoded beam to the remote measurement sites using the optical fibers or other suitable means. Preferably, the timing signals generated by the optical switches described below are dispatched along with the encoded beam such that the data acquired at the remote locations can be properly analyzed.

FIG. 1B is a view of the entrance and exit apertures 32, 44 along the arrow 1B—1B in FIG. 1A. Also shown in FIG. 1A is an xyz axis, so that the view along the arrow 1B—1B is along the negative x axis. A sample and/or optical fiber (not shown) may be placed between the source and the entrance aperture or between the exit aperture 44 and the detector 26 for analysis.

Computer 28 includes an analog to digital converter 28.adc, a sub-signal separator algorithm 28.sss (described below), a decoding algorithm 28.dec, a transient signal detector 28.tsd (described below), an alignment calibration algorithm 28.aca (not shown, described below), an alignment tracking algorithm 28.ata (not shown, described below), a hardware driver 28.drv (not shown, described below), an application specific analytical function 28.asf, and an output 28.out. Preferably, the detectors analog output is sampled by Analog-to-Digital Converter (ADC) 28.adc which is triggered by a first optical switch, 77, comprised of radiation source 154a and photodetector 156a. A second optical switch, 78, comprised of radiation source 154b and photodetector 156b, provides the computer with a reference of 0 degrees to synchronize the output of 28.adc with the decoding algorithm. Preferably, output 28.out includes a connection to the internet, a local area network or a wireless network so that a number of remote instruments can be monitored from a central location. As will be described below, as taught by this invention, the filters in or on modulator 22 are such that the optimum 50% duty cycle is retained and computer 28 can determine the amplitude of each radiation component encoded by modulator 22, without having to solve a simultaneous system of equations for arbitrary radial intensity distributions in target image 52.

An alignment probe, 79, shown in FIG. 1A, comprised of radiation source 154c and photodetector 156c, is positioned such that the alignment beam emitted by 154c and collected by 156c is partially interrupted by the timing marks and/or additional location marks (not shown) on modulator 22. Preferably, the alignment beam is positioned such that the marks at regular angular intervals obscure roughly half of the alignment beam and the marks at non-regular angular intervals obscure roughly the other half of the alignment beam. The analog output of alignment probe 79 is analyzed by alignment tracking algorithm 28.ata to gauge the error in the absolute position of the radiation filters with respect to the axis of rotation. This positional error can arise from the manufacturing process of the modulator (e.g., the modulator pattern is printed off center on the substrate, resulting in a periodic error), from the wobble of the spindle (resulting in a dynamic, periodic or non-periodic error), or from the thermal expansion of the substrate (resulting in a static radial error). Preferably, the output of 28.ata is used as input to the application specific analytical function 28.asf to compensate for the effects of the error in the absolute position of the radiation filters with respect to the axis of rotation. More preferably, the output of 28.ata is used in alignment tracking mechanism 179 (not shown, described below), which dynamically positions one or more optical elements to keep target image 52 properly aligned on modulator 22 as substrate 23 rotates about axis 40. Analyzer 100 also includes alignment calibration mechanism 178 (not shown, described below), which aligns the radiation components with the radiation filters.

Figure 2:
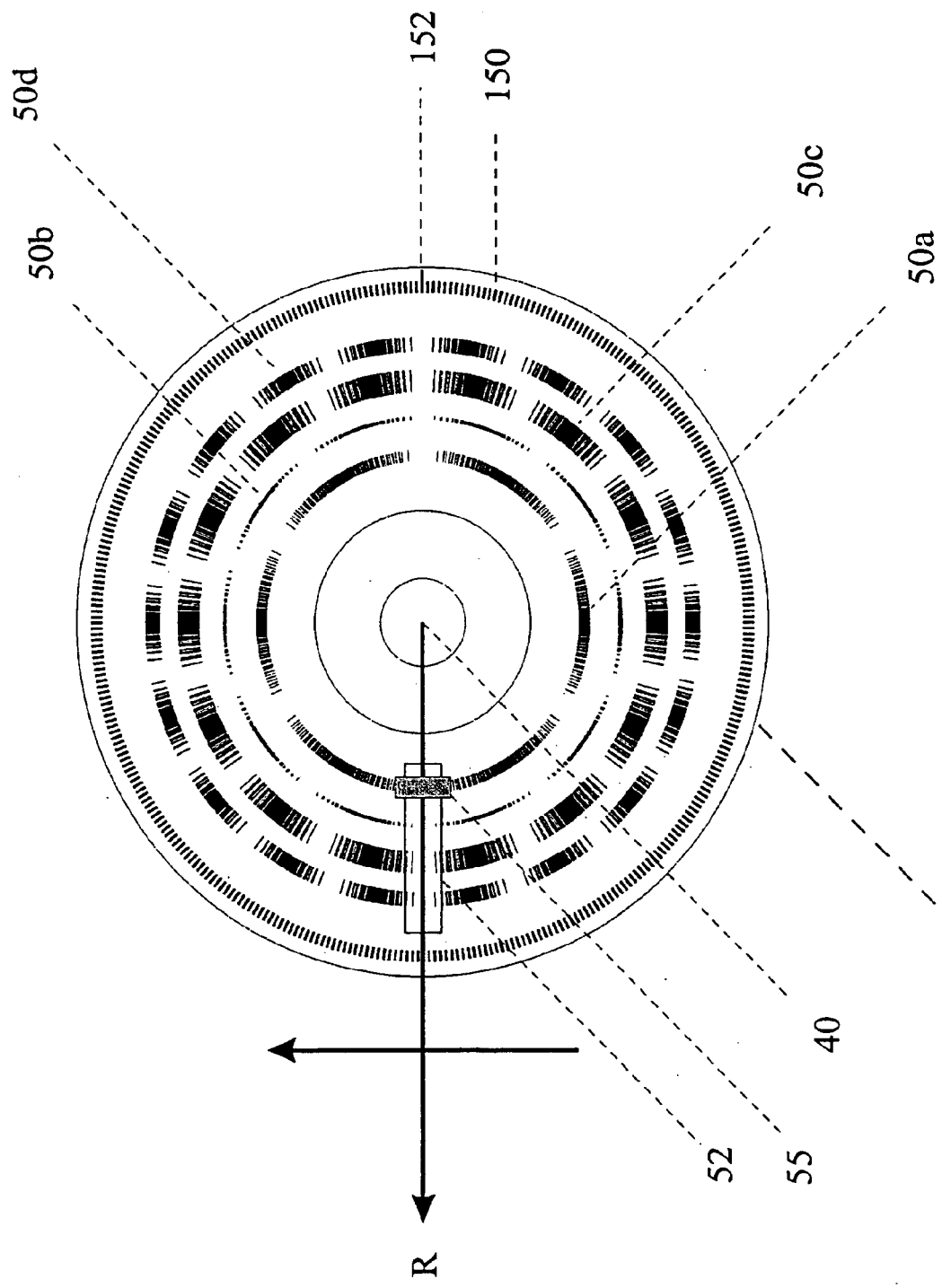
FIG. 2 is a top view of a two-dimensional spatial radiation modulator suitable for use in the analyzer of FIG. 1 to illustrate an embodiment of the invention.

FIG. 2 is a top view of a radiation modulator with four different radiation intensity filters thereon to illustrate an embodiment of the invention. As shown in FIG. 2, modulator 22A includes four radiation filters 50a, 50b, 50c and 50d. These filters may be formed as a patterned layer of radiation reflective material on top of a non reflective substrate, or as a patterned layer of non-reflective material on top of a reflective substrate; alternatively, these filters may be formed as patterned radiation transmissive areas in an opaque substrate or as a patterned layer of opaque material on a transmissive substrate. For convenience in description, the radiation intensity filters are described to reflect radiation, it being understood that radiation intensity filters that transmit instead of reflect radiation or introduce a phase difference may be used instead in each of the embodiments herein and such variations are within the scope of the invention. In modulator 22A, the four radiation filters 50a, 50b, 50c and 50d are centered at non-regular intervals along the radial axis and have different radial widths. In the preferred embodiment, the radial position, radial width and modulation depth of the radiation filters are individually optimized for a particular analytical function 28.asf. Modulator 22A also includes a number of timing marks at regular angular intervals 150 and one or more timing marks at non-regular angular intervals 152.

In the preferred embodiment, the timing marks are reflective and the sources 154a, 154b and 154c and the photodetectors 156a, 156b and 156c are located on the same side of the modulator. In this manner, sources 154a, 154b and 154c and the photodetectors 156a, 156b and 156c can be mounted on the same PC board. Alternately, the substrate is transmissive to the timing beam and timing marks obstruct the timing beam or the substrate is opaque to the timing signal and timing marks are milled or etched through substrate. Therefore, the output of photodetector 156b may supply through a connection to computer 28 to mark the zero rotational angle mark 152 and 156a may supply through a connection to also mark the instances of the passage of each of the timing marks 150. Such instances may be utilized by computer 28 for sampling the output from detector 26 when the disc is rotated about rotation axis 40.

Radiation Intensity Filters

In the preferred embodiment, the radiation filters of the present invention have modulation functions that are digitized approximations, or replicas (e.g., a halftone representation) of the functions $\sin^2(m\theta+p\pi/4)$, wherein m is an integer. Filter 50a, for example, is a digitized approximation of the modulation function $\sin^2(3\theta)$, filter 50b that of modulation function $\sin^2(5\theta)$, filter 50c that of $\sin^2(7\theta)$ and filter 50d that of $\sin(9\theta)$. As shown in FIG. 2, the reflectance or transmittance of each of the radiation filters 50a–50d varies as a distinct function of the rotational angle $\theta$ of modulator 22A around the rotational axis 40. At any given rotational angle of modulator 22A with respect to the target image 50, the amplitude of the modulated radiation is given by the fraction of radiation which is reflected by (or transmitted through) the non-contiguous radiation filter. As modulator 22A is rotated about axis 40 radiation component 52a is focused onto different portions of radiation filter 50a. Thus, as the modulator 22A is rotated, radiation component 52a is encoded by the angle-dependent reflectance of radiation filter 50a.

If we define active area 53a as the overlap of image 52 and the annular region encompassing radiation filter 50a, the relative intensity of the reflected (or transmitted radiation) is given by the ratio of the sum of the areas of the non-contiguous regions of 50a within 53a to the total area of 53a. If the width of the smallest non-contiguous region of 50a along the azimuthal axis, $\Theta$, is equal to one-half the width of target image along the azimuthal axis, the intensity of the incident radiation can be modulated with three substantially distinct levels of contrast as zero, one, or two contiguous regions are moved under target image 52. This is analogous to a two-bit halftone which has reflectance (or transmission) values of $\{0,0.5,1\}$. By using non-contiguous regions with smaller widths relative to the target image width the number of substantially distinct levels of contrast can be increased.

As shown in FIG. 2, radiation intensity filters 50a–50d of modulator 22A resemble concentric barcodes along the azimuthal axis, which are individually engineered to encode a section of target image 52 as a digitized approximation or replica (e.g., a halftone representation) of $\sin^2(m\theta)$ as modulator 22 is rotated about axis 40. Radiation filters 50a–50d are comprised of a plurality of non-contiguous regions having optical properties substantially different from substrate 23, including a number having a spatial extent along the azimuthal axis, $\Theta$, which is substantially smaller the width of the target image 52 along the azimuthal axis. As shown in FIG. 2, the total number of non-contiguous regions comprising the radiation filters of the present invention is greater than the number of local maxima present in the substantially smooth function being replicated. For example, the function $\sin^2(m\theta)$ has 2m local maxima (i.e., where $\sin^2(m\theta)=1$) over the range $\{0,2\pi\}$, but the radiation filters of the present invention require a minimum of 4m non-contiguous regions of at least two different sizes, and with at least two different spacings, to provide a halftone representation of $\sin^2(m\theta)$ over the same interval. The number of levels of contrast or gray scale is substantially equal to one plus the ratio of the target image width to the width of the smallest non-contiguous region along the azimuthal axis, $\Theta$.

The modulation function of the filters on modulator 22A can change in both the radial and azimuthal directions. In the embodiment of FIG. 2, the modulation functions of the filters 50a–50d change only in the azimuthal direction and not in the radial direction. Each of the filters 50a–50d occupies a two-dimensional annular area having a substantially constant radial width. The radiation filters shown in FIG. 2 modulate the intensity of the incident radiation uniformly across the radial width of the encoding channel. As a result, the present invention is immune to modulation waveform distortion resulting from arbitrary radial intensity distributions. If the target image 52 is a dispersed image, the intensities of the spectral components encoded by filters 50a–50d are modulated independent of the bandwidth. If the target image 52 is an image of an extended source, the intensities of the spectral components encoded by filters 50a–50d are modulated independent of the spatial resolution.

In another embodiment of the invention, the "barcode" like structures shown in 50a–50d, which are shown to extend continuously across the radial width of the radiation filter, are broken up to control the modulation depth and/or to increase the number of distinct levels of contrast available. This embodiment may be useful for improving orthogonality or to control the modulation depth on a channel-by-channel basis independent of the bandwidth, which may be useful for balancing signal levels in systems where one or more channels have a disproportionately large fraction of the total incident radiation. Preferably, sequential "barcode" like structures in the radiation filter will be broken up in a "checker-board" like pattern to control the modulation depth and/or increase the number of available levels of contrast while substantially precluding waveform distortion resulting from arbitrary radial intensity distributions.

In the preferred embodiment, the radiation filters 50a–50d on modulator 22A are comprised of an annular region substantially encompassing a plurality of pixels having optical characteristics substantially different from the substrate. The pixels are patterned substantially within the annular region to modulate the intensity of a corresponding component predominantly along an azimuthal axis to provide an encoded component, wherein the amplitude of the encoded component changes between three or more substantially distinct levels of contrast as the substrate is rotated about rotation axis 40. Instead of using a substrate with low reflectivity or transmission and a patterned layer of high reflectively material on the substrate as described above, (or forming patterned transmissive areas in an opaque substrate), the radiation filters may be constructed in a different manner. Thus a substrate with moderate reflectivity or transmission may be employed instead. Then in areas of the filters requiring high reflectivity or transmission, an area having such characteristics is formed (by deposit of a reflective layer or formation of transmissive area), and a layer of low reflectivity or translucidity material may be deposited in areas of the filter calling for such characteristics.

Instead of using patterns of alternating high and low reflectance or transmission, it is also possible to construct the modulators with substantially orthogonal modulation functions that are not digitized but are "analog" in nature. Thus neutral density filters may be used for this purpose, where the filters are formed by sputtering a radiation reflective material onto a non-reflective or transparent substrate. Depending on the thickness of the material sputtered, the amount of transmission or reflection can be controlled to achieve a substantially continuous and smooth intensity modulation function. In this embodiment, the radiation filters have substantially continuously variable optical characteristics along an azimuthal axis, and the optical characteristics are continuously varied to modulate the intensity of a corresponding component as a substantially smooth function of a rotation angle of the modulator about the rotation axis.

Figure 3A:
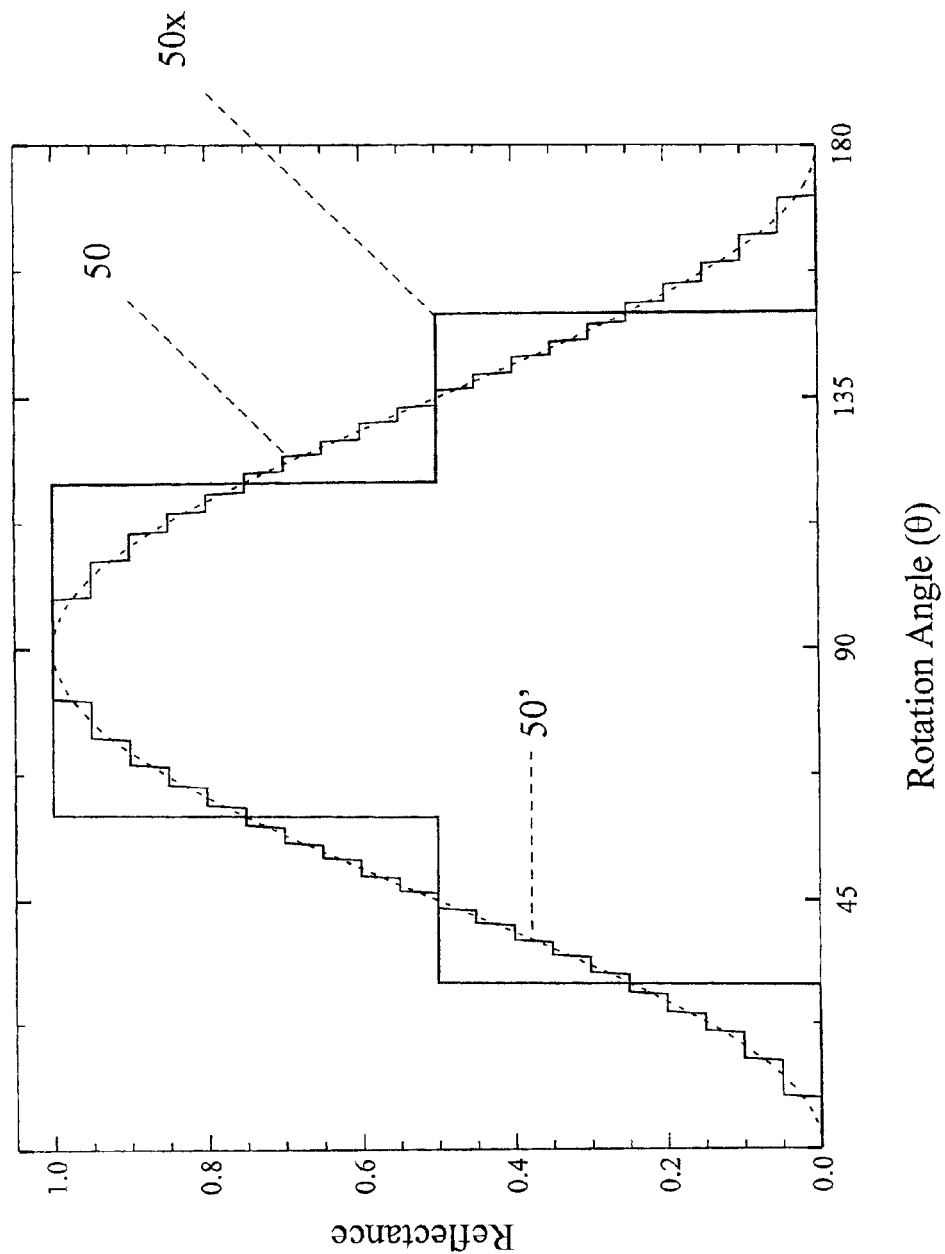
FIG. 3A is a graphical plot of a digitized replica of a smooth modulation function of one of the dispersed radiation filters in the modulator of FIG. 2 and an idealized modulation function from which the digitized modulation function of the filter of the modulator in FIG. 2 can be derived. Shown also in FIG. 3A is a digitized modulation function with only three levels of gray scale as a coarse digitized replica of the idealized modulation function of FIG. 3A.

FIG. 3A illustrates one possible digitized approximation 51 to the $\sin^2(m\theta+p\pi/4)$ function with m=1 and p=0 which is obtained by rounding $\sin^2(\theta)$ up or down using 20 levels of contrast or gray scale. Also shown is the digitized approximation to the $\sin^2\theta$ with three levels of gray scale, 51×. In general, the more levels of gray scale the closer is the digitized approximation to the idealized modulation function $\sin^2(\theta)$ which is shown in dotted line 50'. Obviously, other digitized approximations of the idealized function 50' may be employed and are within the scope of the invention. The digitized approximations are adequate when it is possible to differentiate the contribution to the detector signal caused by the various encoded components without having to solve a simultaneous system of equations, and may include a small but finite number of corrections to compensate for the effects of digitization.

Figure 3B:
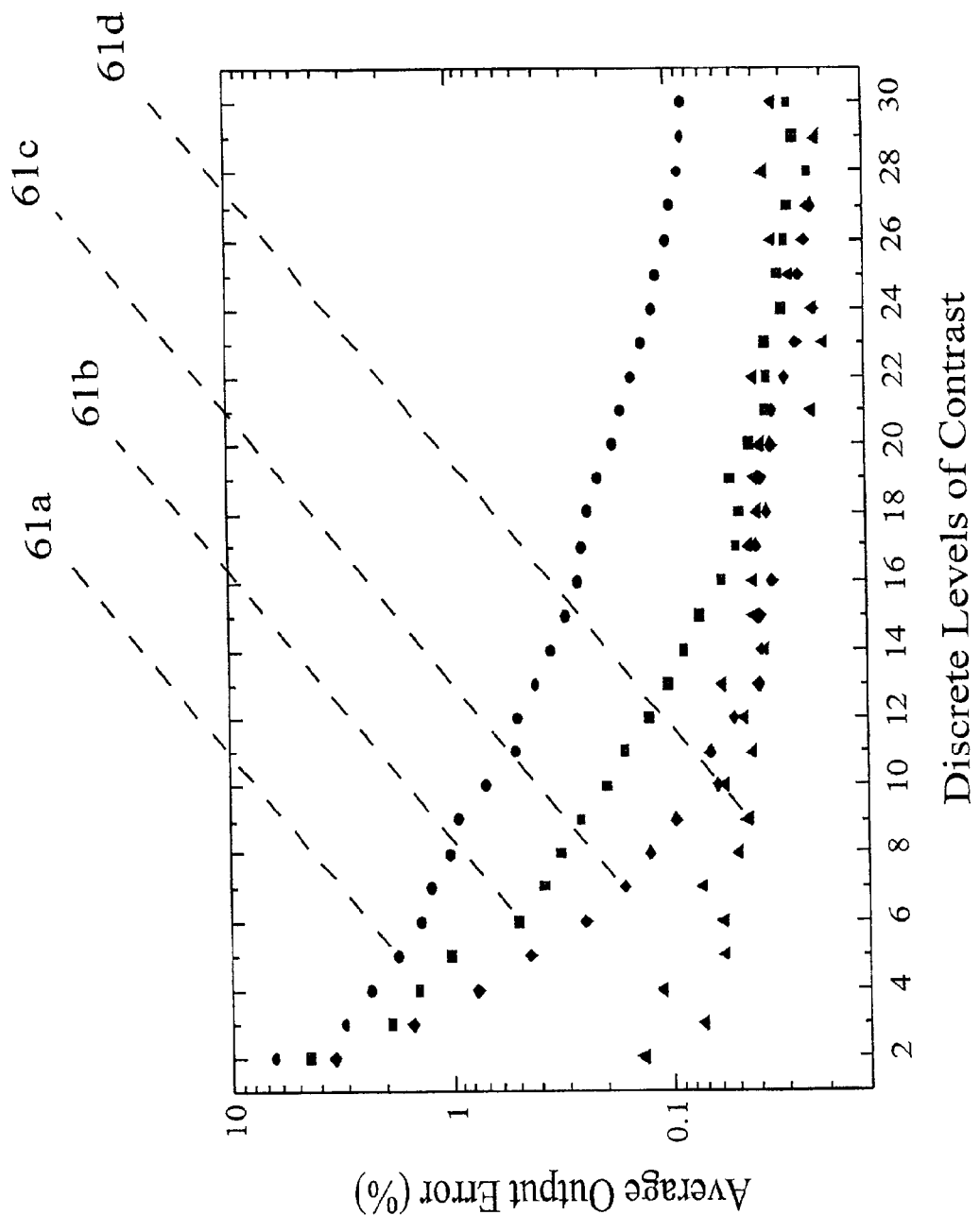
FIG. 3B is a plot showing the effects of finite digitization on the nominally orthogonal amplitude wavefunctions, $\sin^2(m\theta+p\pi/4)$. The data points were obtained for a twenty-five channel system, where p=0, and m=1 through 25.

FIG. 3B is a plot showing the effects of finite digitization on the nominally orthogonal amplitude wavefunctions, $\sin^2(m\theta+p\pi/4)$. The data points were obtained for a twenty-five channel system, where p=0, and m=1–25. A difference in the decoded amplitudes is defined by normalizing the twenty-five amplitudes to unity, decoding the amplitudes a first time, and then varying the amplitude of a single channel and decoding the amplitudes a second time. The average output error is given by the sum of the absolute difference in the first and second decoded amplitudes divided by the number of channels. In the FIGURE, 61*a*, 61*b* and 61*c* are the resulting errors for varying the amplitude of the fundamental, m=1, the first harmonic, m=2, and the second harmonic, m=3 by +/−100%. The error for varying the amplitude of the m=11 term is also shown by 61*d*. The figure clearly illustrates the effects of finite digitization on the orthogonality of the modulation wavefunctions. Low end applications may only require 3–10 levels of contrast to meet a given accuracy specification, but high end systems, where significant accuracy is required may require 100 or more levels of contrast. For the most demanding applications, the first-order amplitude correction described below may be used to correct the decoded amplitudes for the interference.

As noted above, many of the advantages of the invention stem from the fact that it is possible to choose filter modulation functions that retain the optimum 50% duty cycle and to decode the detector signal to obtain the respective amplitudes of two or more encoded components without having to solve a simultaneous system of equations. For many applications, this is possible where the modulation functions are roughly orthogonal. For some applications requiring very high accuracy, it may be useful to define substantial orthogonality as follows. The modulation functions of two radiation filters may be considered to be substantially orthogonal to each other when changing the amplitude of the first (second) encoded component by 100% results in an error in the decoded amplitude of the second (first) component of less than one part in 1000 after applying the first-order amplitude correction as described below.

Target Images

Figure 4A:
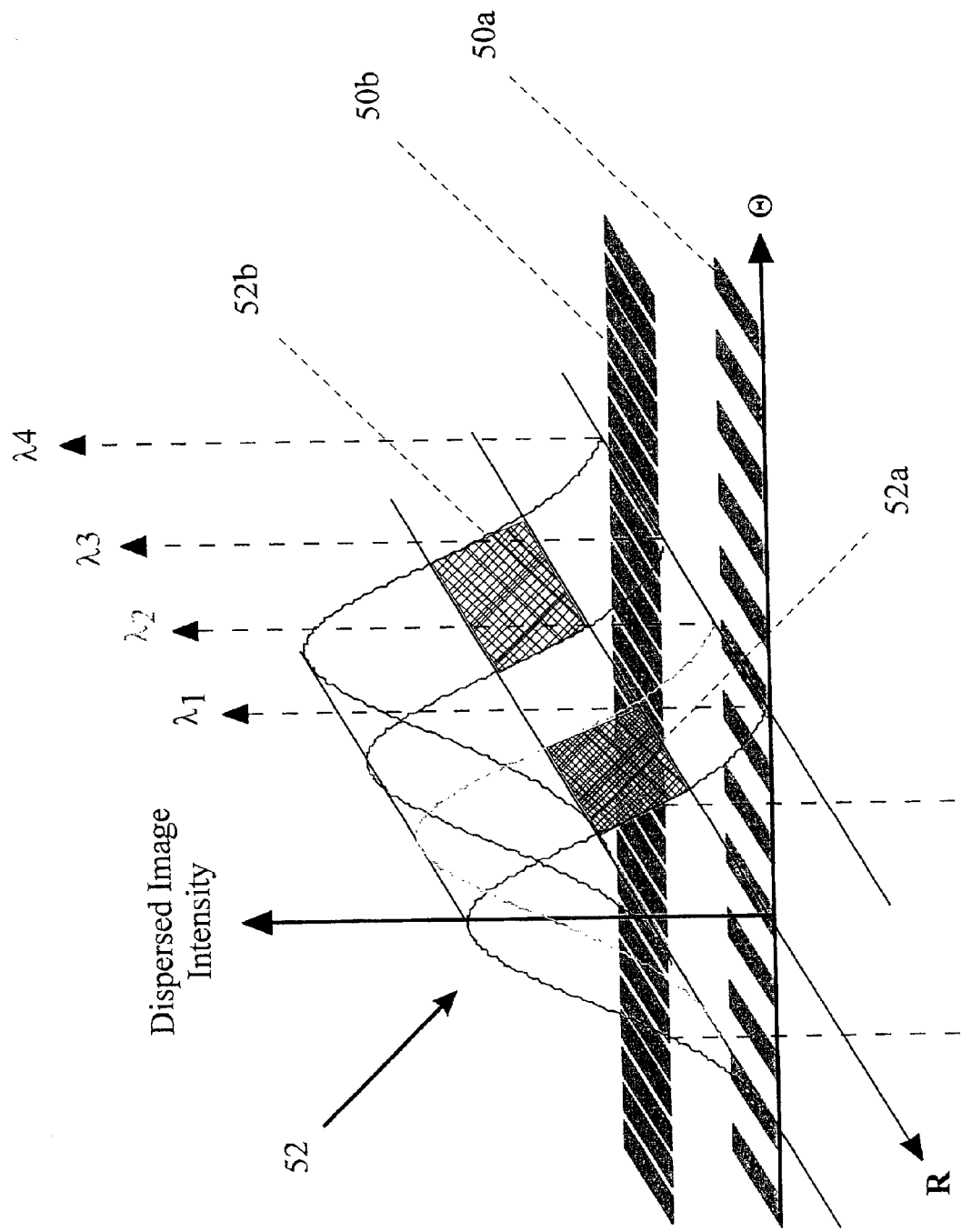
FIG. 4A is an illustration of the focal plane of the radiation analyzer of FIG. 1 configured as a spectrum analyzer, showing a dispersed image superposed upon the radiation filters of the two-dimensional modulator of FIG. 2.
Figure 4B:
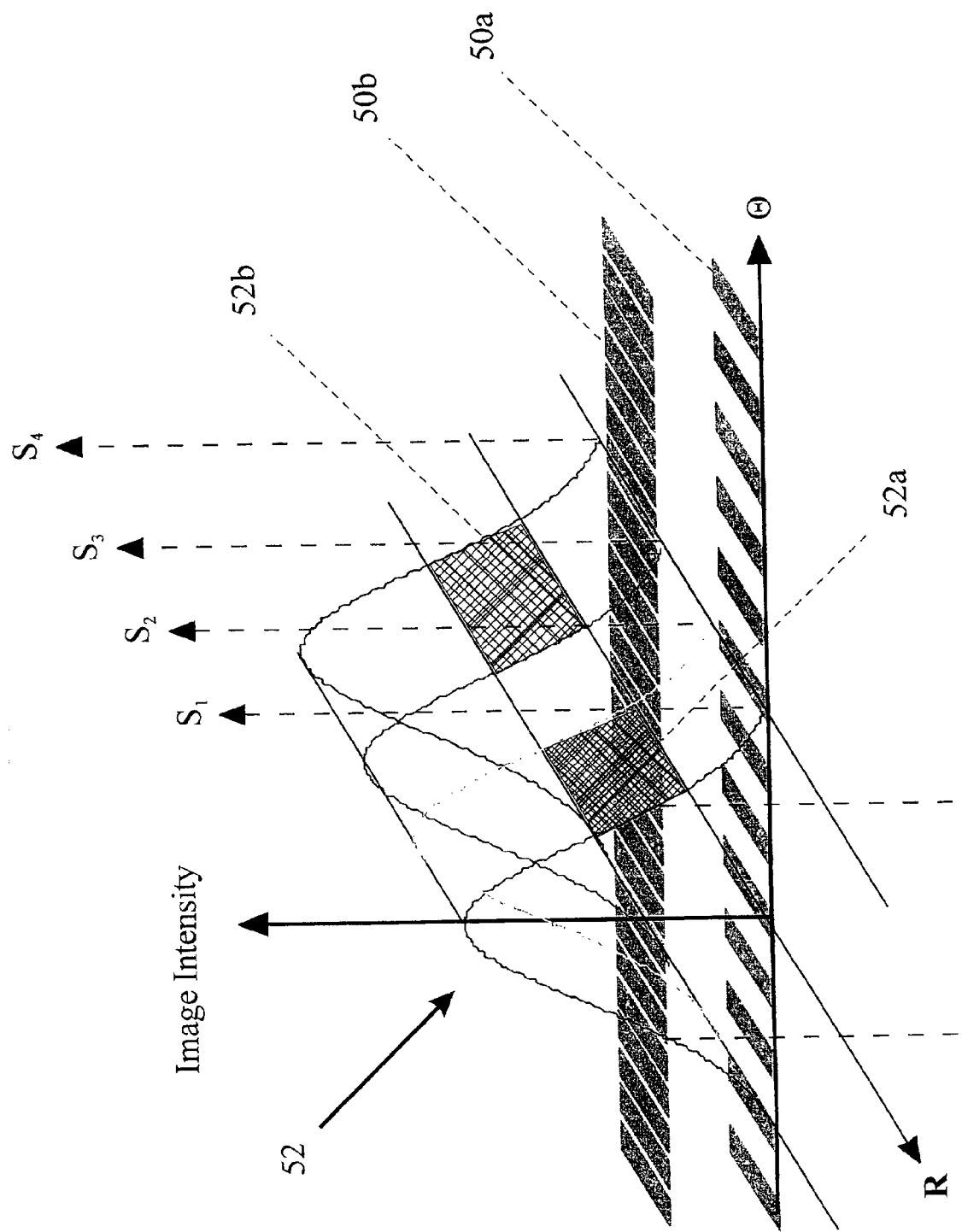
FIG. 4B is an illustration of the focal plane of the radiation analyzer of FIG. 1 configured as an image analyzer, showing an image of an extended source superposed upon the radiation filters of the two-dimensional modulator of FIG. 2.

FIG. 4A and FIG. 4B are illustrations of target image 52 which is formed by pre-encoder optic 36A of FIG. 1A onto modulator 22 to illustrate the invention. As noted above, the target image is either a dispersed image with different spectral components focused at different points along an encoding axis, or a extended image with different spatial components focused at different points along an encoding axis. For simplicity, only filters 50*a* and 50*b* of FIG. 2 are shown schematically in FIG. 4A and FIG. 4B. Preferably, as shown in FIG. 4, the encoding axis is substantially along the radial axis, R, of modulator 22. The target image width is defined as the spatial extent perpendicular to the encoding axis.

In FIG. 4A we illustrate the case where target image 52 is a dispersed image of a broadband or multiple wavelength source with its dispersion axis along the radial axis, R. Two different spectral components, 52*a* and 52*b*, which are encoded by modulator 22B, are shown by different cross-hatching in FIG. 4A. Spectral component 52*a* is characterized by a center wavelength $(\lambda_2+\lambda_1)/2$ and a bandwidth $(\lambda_2-\lambda_1)$. Similarly, spectral component 52*b* is characterized by a center wavelength $(\lambda_4+\lambda_3)/2$ and a bandwidth $(\lambda_4-\lambda_3)$. Examples of broadband or multiple wavelength radiation sources include blackbody radiators, incandescent lamps, light-emitting diodes, low-pressure gas lamps, optically, biologically or chemically excited samples, dye lasers, semiconductor lasers, glass lasers, gas lasers, multi-wavelength optical fibers, hot gas and/or vapor streams, furnaces and reflected or filtered sunlight.

In FIG. 4B we illustrate the case where target image 52 is an extended image (i.e., the image of an extended source). In this case we simplify identify 52*a* and 52*b* as two different spatial components of the extended source and $s_1$ and $s_2$ define the spatial boundaries of 52*a*, and $s_3$ and $s_4$ define the spatial boundaries of 52*b*. One example of an extended source is a collection of different samples which emit, scatter, transmit or reflect radiation in response to an excitation. In this case, the spatial components 52*a* and 52*b* correspond to the radiation emitted, scattered, transmitted or reflected by a particular sample in the collection. A second example of an extended source is a linear array of optical fibers. In this case, the spatial components 52*a* and 52*b* correspond to the radiation emitted or reflected by a particular fiber in the array. A third example of an extended source is radiation transmitted through a collection of bandpass filters or a linear variable filter. In this case, spatial components 52*a* and 52*b* correspond to radiation transmitted through or reflected from two different bandpass filters in the collection or two different portions of the linear variable filter. A fourth example of an extended source is a collection of radiation sources, (e.g., a linear array light emitting diodes or laser diodes). In this case, the spatial components 52*a* and 52*b* correspond to the radiation emitted by the individual sources comprising the collection. Other examples of extended sources include semiconductor wafers and circuits, mechanical assemblies, a multi-mode optical fiber, a multi-lane electrophoresis, an interference pattern, and reflected or filtered sunlight collected over an extended area.

Decoding Algorithm

At any given rotation angle, the total signal incident on detector 26 in FIG. 1A is given by the sum of the sub-signals arising from the selected radiation components, 52*a*–52*d*, independently encoded by the angle-dependent reflectance of their corresponding radiation filters, 50*a*–50*d*, on modulator 22. In general, the radiation filters can be defined by specifying the values for m and p in the expression $\sin^2(m\theta+p\pi/4)$, where m is an integer. Thus in general, the intensity of the encoded beam detected by detector 26 in FIG. 1A from a radiation modulator such as modulators 22A or other modulators described in this application can be given in general by the following equation:

$$S(\theta) = \sum_m \sum_p a_{m,p} \sin^2\left(m\theta + \frac{p\pi}{4}\right) \tag{1}$$

where $S(\theta)$ is the intensity detected by the detector 26, and the summations include all of the m and p values corresponding to the filters present in a given modulator design. In equation (1), $a_{m,p}$ is the amplitude of the encoded component that has been encoded by the radiation filter having a modulation function which is a digitized approximation or replica (e.g., a halftone representation) of $\sin^2(m\theta+p\pi/4)$. This invention permits one to retain the optimum 50% duty cycle and to determine the amplitudes of the encoded components without solving a simultaneous system of equations for encoding channels having arbitrary radial width and target images having arbitrary radial intensity distributions. In the summation process in equation (1), the filters present in a particular modulator may not include filters corresponding to all combinations of m and p values. This is exemplified in the modulator 22A of FIG. 2 where p takes on only the value 0, and in the modulator 22B of FIG. 5 where m takes on the value 3 throughout all the filters. In such event, the amplitude $a_{m,p}$ for filters that are not present in the modulator is simply 0. Preferable, decoding algorithm 28.dec is provided with a list of the m and p values patterned onto the modulator and the summation in equation (1) is restricted to the list. More preferably, the list is encoded onto the disc so that the correct list is always used by 28.dec to decode the detector signal.

As a further benefit, the present invention enables the use of generalized approaches for the modulator drive system, data acquisition and the decoding algorithms. For example, motorized spindle 42 is rotated at a roughly constant frequency (as opposed to being stepped), the detectors analog output is sampled by Analog-to-Digital Converter (ADC) 28.adc which is triggered by optical switch 77 in response to timing marks 150. Optical switch 78 responding to timing mark(s) at non-regular angular intervals 152, provides computer 28 with a reference of 0 degrees to synchronize the output of 28.adc with the decoding algorithm 28.dec. Hence, the decoding algorithm is compatible with any function defined in equation (1), and the number and identity {m,p} of the modulated components, and the specific analytic functions to be performed on the decoded data are defined in application specific software. Preferably, the list of {m,p} values corresponding to the radiation filters on the modulator are encoded onto the disc.

The trigonometric functions $\sin^2(m\theta+p\pi/4)$ obey the following orthonormal relation.

$$\int_0^{2\pi} d\theta \cos\left(2m\theta + \frac{p\pi}{2}\right)\sin^2\left(n\theta + \frac{q\pi}{4}\right) = -\frac{\pi}{2}\delta_{m,n}(\delta_{p,q} - \delta_{p,q\pm 2}) \quad (2)$$

The amplitudes $a_{m,p}$ of the encoded spectral components may be determined using the orthogonal properties of the trigonometric functions in accordance with equation (3) below:

$$a_{m,p} = -\frac{2}{\pi}\int_0^{2\pi} d\theta \cos\left(2m\theta + \frac{p\pi}{2}\right)S(\theta) \quad (3)$$

First-Order Amplitude Correction

One complication introduced by the use of digitized approximations or replicas of the trigonometric functions $\sin^2(m\theta+p\pi/4)$, is that the orthogonality described by equation (2) and used in equation (3) above is inexact. As a result, in some applications it may be necessary for the interference terms to be accounted for and the individual amplitudes corrected for the interference resulting from the other channels, which naturally leads to a series of successively higher-order correction terms:

$$a_{m,p} = a_{m,p}^{(0)} + a_{m,p}^{(1)} + \ldots \quad (4)$$

where the zero-order amplitude coefficients are determined from $$a_{m,p}^{(0)} = -\frac{2}{\pi}\int_0^{2\pi} d\theta \cos\left(2m\theta + \frac{p\pi}{2}\right)S(\theta) \quad (5)$$

The first-order amplitude correction is given by $$a_{m,p}^{(1)} = \sum_n \sum_q A_{m,p}^{n,q} a_{n,q}^{(0)} \quad (6)$$

where it is understood that the term in the summation where n=m and q=p is excluded.

In equation (6), the matrix elements are determined by sequentially decreasing or enhancing the amplitudes of the $a_{n,q}$ and measuring the changes in $a_{m,p}^{(0)}$. For example, if we identify $\delta a_{m,p}^{(0)}$ as the observed change in $a_{m,p}^{(0)}$ resulting from $\Delta a_{n,q}^{(0)}$, the imposed change on $a_{n,q}^{(0)}$, the corresponding matrix element is given by $$A_{m,p}^{n,q} = \frac{\delta a_{m,p}^{(0)}}{\Delta a_{n,p}^{(0)}} \quad (7)$$

Preferably, the imposed change on $a_{n,q}^{(0)}$ is facilitated by a movable mask having an aperture or obscuration 55, which is comparable in size to the radial width of the radiation filters, where the mask is translated along the radial axis of modulator 22 such that the incident radiation is selectively transmitted or blocked from the radiation filters in sequence. For example, a disc with a spiral aperture or obscuration 55, which is mounted in a plane parallel to modulator 22, directly above or below modulator 22, and is stepped about rotation axis 40. More preferably, the imposed change on $a_{n,q}^{(0)}$ is facilitated by a dedicated radiation source and a dedicated detector which are independently or collectively translated along the radial axis of modulator 22 such that the incident radiation is selectively modulated by the radiation filters in sequence. Most preferably, the beam size of the dedicated radiation source along the radial axis is substantially smaller than the radial width of the narrowest radiation filter on modulator 22. In this manner, the modulated components can be isolated from one another to more accurately determine their respective harmonic contents.

In practice, the integral shown in equation (5) is replaced with a discrete summation over M, the number of Data Acquisition (DAQ) events (or intervals, steps or cycles) per rotation. On start-up, a trigonometric look-up table, is defined and initialized with the values of $\cos(2m\theta+p\pi/2)$ evaluated at the DAQ intervals for rotation $$T_{m,p}^j \equiv -\frac{2}{\pi M}\cos\left(\frac{4jm\pi}{M} + \frac{p\pi}{2}\right) \quad (8)$$

The zeroth-order amplitude coefficients are given by a summation of the discrete signal measurements multiplied by the corresponding entry in the trigonometric look-up table $$a_{m,p}^{(0)} = \sum_{j=1}^M T_{m,p}^j S(j) \quad (9)$$

where S(j) is the ADC reading from the detector at the jth DAQ step; i.e., the output from 28.adc. At the end of a complete rotation, the first-order amplitude corrections are evaluated if required for a given application:

$$a_{m,p}^{(1)} = \sum_n \sum_q A_{m,p}^{n,q} a_{n,q}^{(0)} \qquad (10)$$

where it is understood that the term in the summation where n=m and q=p is excluded. Note that if the amplitudes have not changed significantly since the last time the corrections were evaluated, the corrections need not be re-evaluated.

Transient Signal Detection

Preferably, computer 28 in FIG. 1 includes a transient signal detection algorithm 28.tsd to detect transients in the signal levels of the encoded components which occur during a rotational period of modulator 22. More preferably, the computer will analyze the transient signal to determine its harmonic content. At each DAQ step j, transient signal detection algorithm 28.tsd subtracts the detector signal from one or more previous detector signals or the expected signal calculated using the last calculated zeroth-order amplitude coefficients defined by equation (9) above:

$$\Delta S^k(j) = S^k(j) - \left\{ \sum_m \sum_p a_{m,p}^{(k-1)} \sin^2\left(\frac{2jm\pi}{M} + \frac{2\pi}{4}\right) \right\} \qquad (11)$$

where $S^k$ (j) is the output from 28.adc (i.e., the detector signal) measured at the jth step on the kth rotational period and the $a_{m,p}^{(k-1)}$ are the zeroth-order amplitude coefficients calculated for the (k−1)th rotational period. The magnitude of $\Delta S^k(j)$ is used to detect amplitude transients in one or more encoded components which occur on a sub-rotational-period time scale. Preferably, when the magnitude of $\Delta S^k(j)$ exceeds a predefined threshold, 28.tsd directs the analyzers operating system to increase the speed of the motorized spindle 42, and when the magnitude of $\Delta S^k(j)$ drops below a second predefined threshold for a predefined extended period of time, 28.tsd directs the analyzers operating system to decrease the speed of the motorized spindle 42. In that way, the motorized spindle 42 can be run a slow as possible, thereby increasing the operating life. Most preferably, $\Delta S^k(j)$ is analyzed by 28.tsd over a sufficient number of DAQ cycles to determine its harmonic content, which in turn will be used as input by the decoding algorithm to compensate for the harmonic interference resulting from sub-period signal transients. Control of motorized spindle 42 may be accomplished by means of computer 28 via a control signal line to motorized spindle 42.

Modulator Patterns

Figure 5:
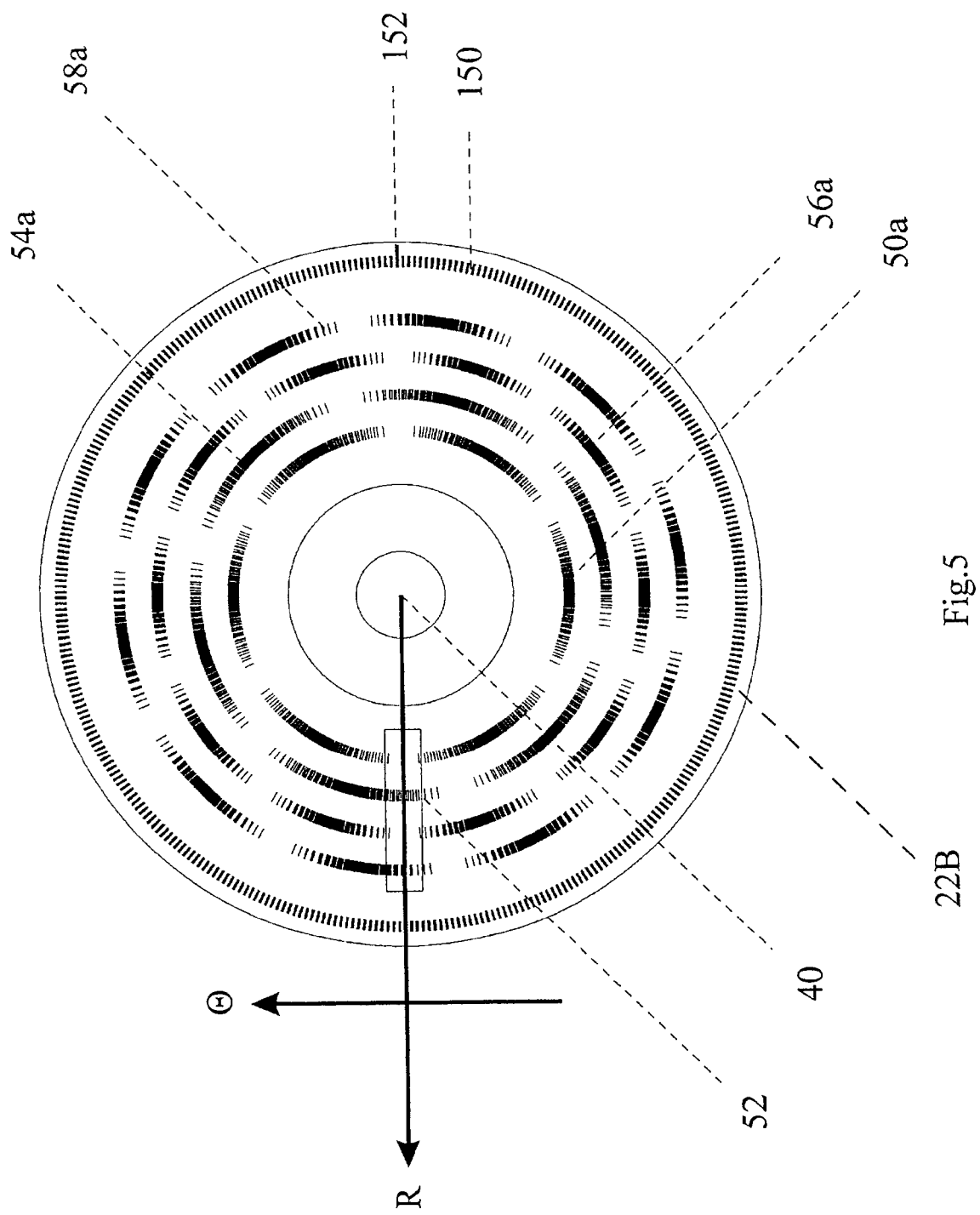
FIG. 5 is a top view of a two-dimensional spatial radiation modulator to illustrate a modulator with four dispersed radiation filters for encoding different radiation components using different modulation functions that are orthogonal to one another.

FIG. 5 is a top view of a radiation modulator 22B to illustrate another aspect of the invention. Modulator 22B is provided with four radiation filters 50a, 54a, 56a and 58a, where the modulation functions of the four filters are all digitized approximations of the function of the general form $\sin^2(m\theta+p\pi/4)$ described above in reference to modulator 22A of FIG. 2. In modulator 22B of FIG. 5, radiation filters 50a and 54a both have m values of 3, but p values of 0 and 1, respectively. Similarly, filters 56a and 58a both have m values of 5, but p values of 0 and 1, respectively. By inspection of the orthogonality relation defined in equation (2), it is clear that all four radiation filters on modulator 22B are substantially orthogonal to one another. The highest harmonic (m value) that can be patterned on a modulator is determined by the size of the image along the azimuthal axis and the circumference of the modulator at the chosen radius. By using filter pairs with the same m values but having p values which differ by an odd integer, the number of orthogonal filters up to any given harmonic can be doubled.

Figure 6:
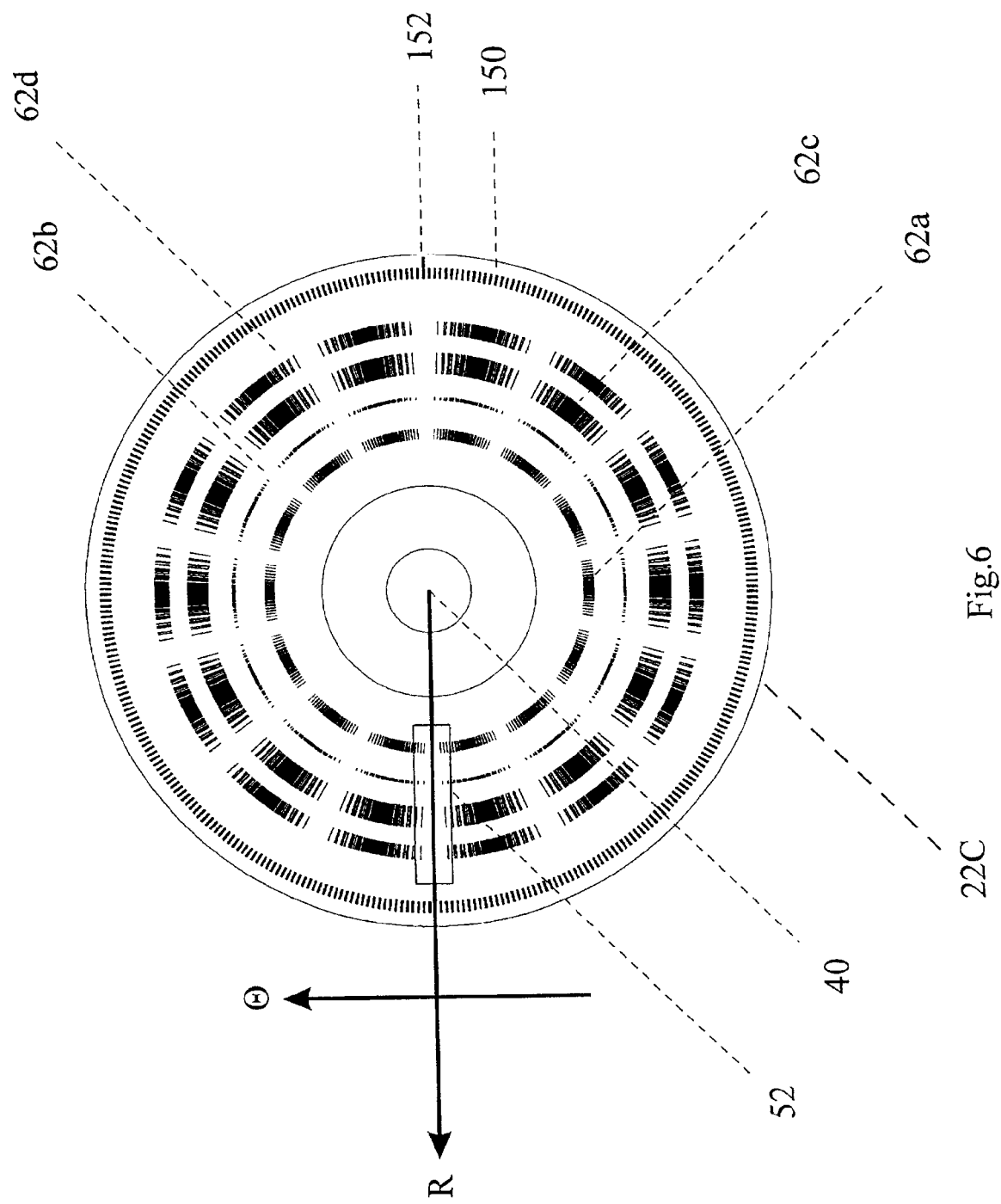
FIG. 6 is a top view of a spatial radiation modulator having four spatial radiation filters for encoding four non-contiguous radiation components using the same modulation function.

FIG. 6 is a top view of a radiation modulator 22C to illustrate another aspect of the invention. Modulator 22C is patterned with four radiation filters therein with the same modulation function (i.e., $\sin^2(m\theta+p\pi/4)$ with identical m and p values), but located at different radii from the rotational axis 40 and separated from one another for encoding different radiation components. In this manner, groups of non-contiguous radiation components can be collectively modulated to enhance the signal-to-noise ratio of the analyzer.

Figure 7:
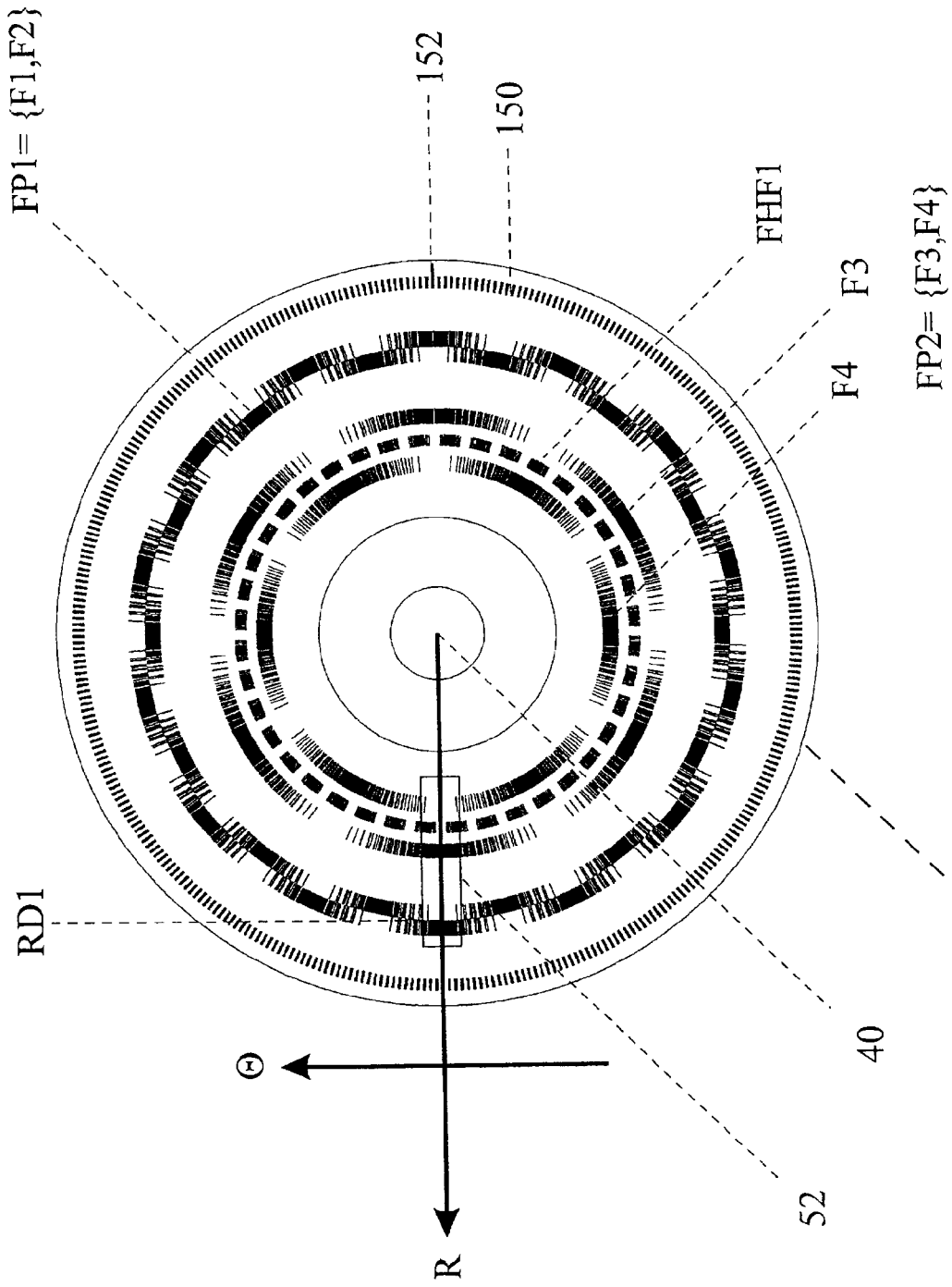
FIG. 7 is a top view of a spatial radiation modulator provided with two pairs of radiation filters for measuring the difference in the radiation intensity incident on the two filters comprising the pair to illustrate another aspect of the invention.

FIG. 7 is a top view of a radiation modulator 22D to illustrate another aspect of the invention. Modulator 22D is patterned with two radiation filter pairs, FP1 comprised of radiation filters {F1,F2}, and FP2 comprised of radiation filters {F3,F4}, and a single non-paired radiation filter FHF1. In modulator 22D, filter pairs FP1 and FP2 are designed to measure the difference in radiation intensity incident on the two filters comprising the pair, {F1,F2} and {F3,F4}, respectively. The modulation functions of the filters comprising each filter pair are complementary or out of phase so that the amplitude and phase of the encoded component is determined by the relative proportion of radiation incident on the two filters. In modulator 22D, the modulation functions of the filters are all digitized approximations of the general form $\sin^2(m\theta+p\pi/4)$. For modulation functions of the form $\sin^2(m\theta+p\pi/4)$, the complementary configuration requires that both filters comprising the pair have the same m value, but different p values, where the difference in p values is an even integer.

In reference to FP1 of FIG. 7, filters F1 and F2 are adjacent to one another. In this manner, the resulting signal from FP1 is substantially equivalent to the derivative of the intensity distribution with respect to radial position evaluated at the border radius, RD1. In one embodiment, the amplitude of the encoded component resulting from filter pair NP1 is nulled or zeroed by balancing the intensity of the radiation which is incident on F1 and F2.

In reference to FP2 in FIG. 7, filters F3 and F4 are separated from one another along the radial axis. The amplitude and phase of the resulting encoded component is determined by the relative proportion of the radiation incident on the two filters. In this manner, the difference in intensity of two radiation components which are separated along the radial axis can be measured directly. In many applications, the analytical function 28.asf in FIG. 1A, requires knowledge of the intensities of the components encoded by F3 and F4, not just the difference in intensity. In modulator 22D, filter FHF1 is designed to provide the absolute intensity at the midpoint between F3 and F3. The modulation frequency (m value) of FHF1 is chosen to be much higher than the modulation frequency of FP2 so that the signal originating from FHF1 can be filtered out using an appropriate electronic bandpass filter 28.bpf between the detector 26 and the analog to digital converter 28.adc. Preferably, the electronic bandpass filter 28.bpf in FIG. 1 has a programmable passband such that the signal originating from FHF1 can be switched in and out of the signal path to 28.adc as needed. In this manner, the absolute intensity associated with filter pair FHF1 can be measured during a calibration cycle and subsequently, the intensity difference obtained from FP2 can be used to enhance the instruments resolution and/or preserve the dynamic range of 28.adc. In the alternative, the signal from detector 26 can be split into two signal paths with different electronic bandpass filter, and a first ADC can be used to measure the component encoded by FP2 and a second ADC can be used to measure the component encoded by FHF1.

Figure 8:
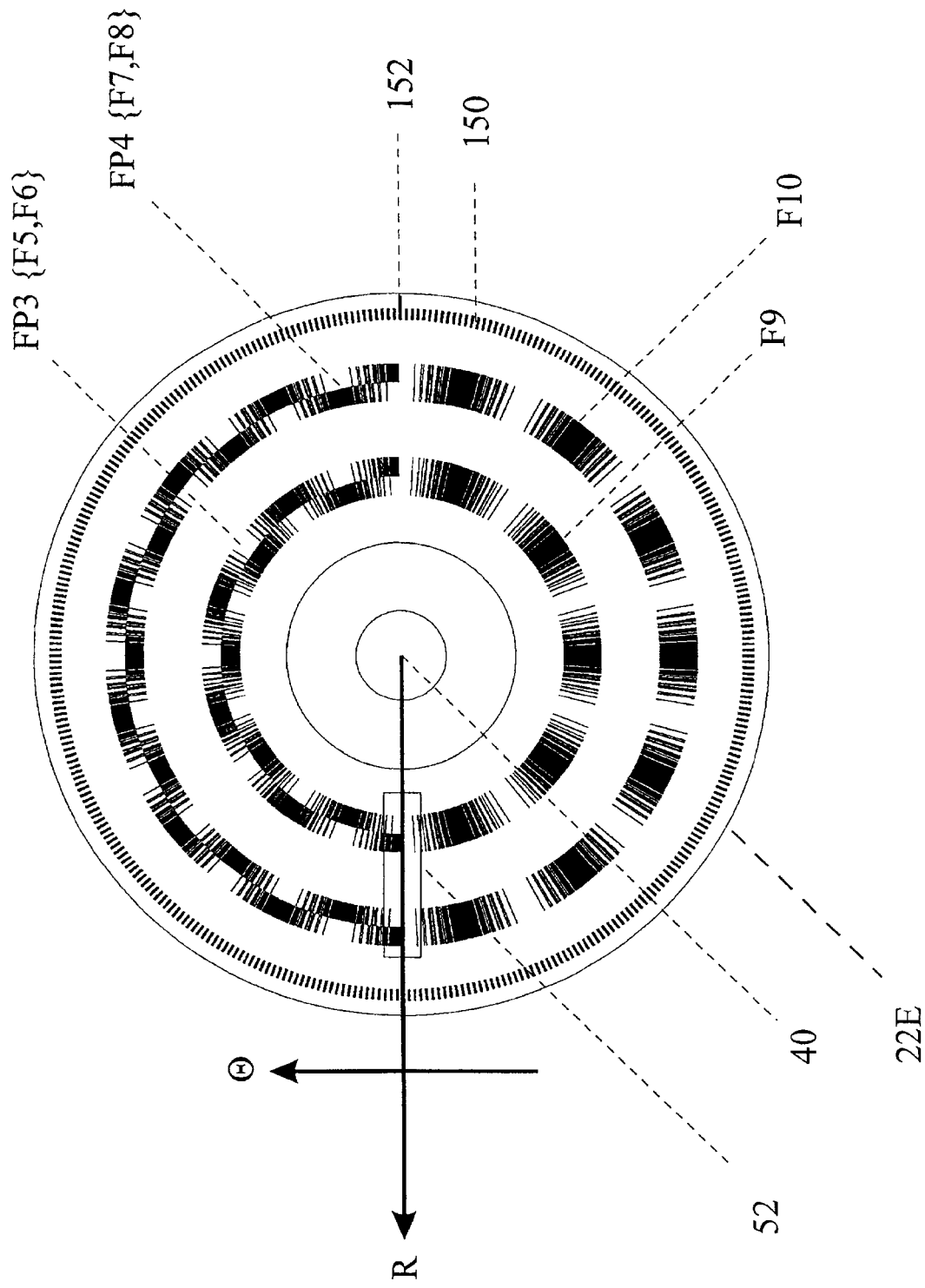
FIG. 8 is a top view of a spatial radiation modulator having two complementary radiation filter pairs for measuring the difference in the radiation intensity incident on the two filters comprising the pair, and two non-paired radiation filters to measure the sum of the radiation intensity incident on incident on the two filters to illustrate another aspect of the invention.

FIG. 8 is a top view of a radiation modulator 22E to illustrate another aspect of the invention. Modulator 22E is provided with two radiation filter pairs, FP3 and FP4, for measuring the difference in the radiation intensity incident on the two filters comprising the pair. Modulator 22E is also provided with two non-paired radiation filters, F9 and F10, for measuring the sum of the radiation intensity incident on the annular region encompassing FP3 and FP4, respectively. The encoded components resulting from FP3 and FP4 are orthogonal to one another, and the encoded components resulting from F9 and F10 are also orthogonal to one another. In FIG. 8, FP3 and F9 occupy the same annular region, with FP3 occupying the upper half of modulator 22E and F9 occupying the lower half of modulator 22E. Similarly, FP4 and F10 occupy the same annular region, with FP4 occupying the upper half of the modulators and F10 occupying the lower half of the modulator. As modulator 22E is rotated counter-clockwise, the target image 52 is encoded by FP3 and FP4 for the first half period of rotation and by F9 and F10 for the second half period of rotation. Computer 28 in FIG. 1A would use sub-signal separator algorithm 28.sss to separate the detector signal into two sub-signals corresponding to {FP3,FP4} and {F9, F10}, respectively. These two sub-signals would be processed by decoding algorithm 28.dec to determine the amplitudes of the encoded components. In this manner, both the derivative of the intensity distribution with respect to radial position evaluated at the border radius and the total intensity of each encoded radiation component can be measured substantially simultaneously. Modulator 22E incorporates a special case of modulation functions based on one or more incomplete rotation periods of modulator 22 (see description below).

Calibration and Alignment Tracking Mechanisms

Figure 9A:
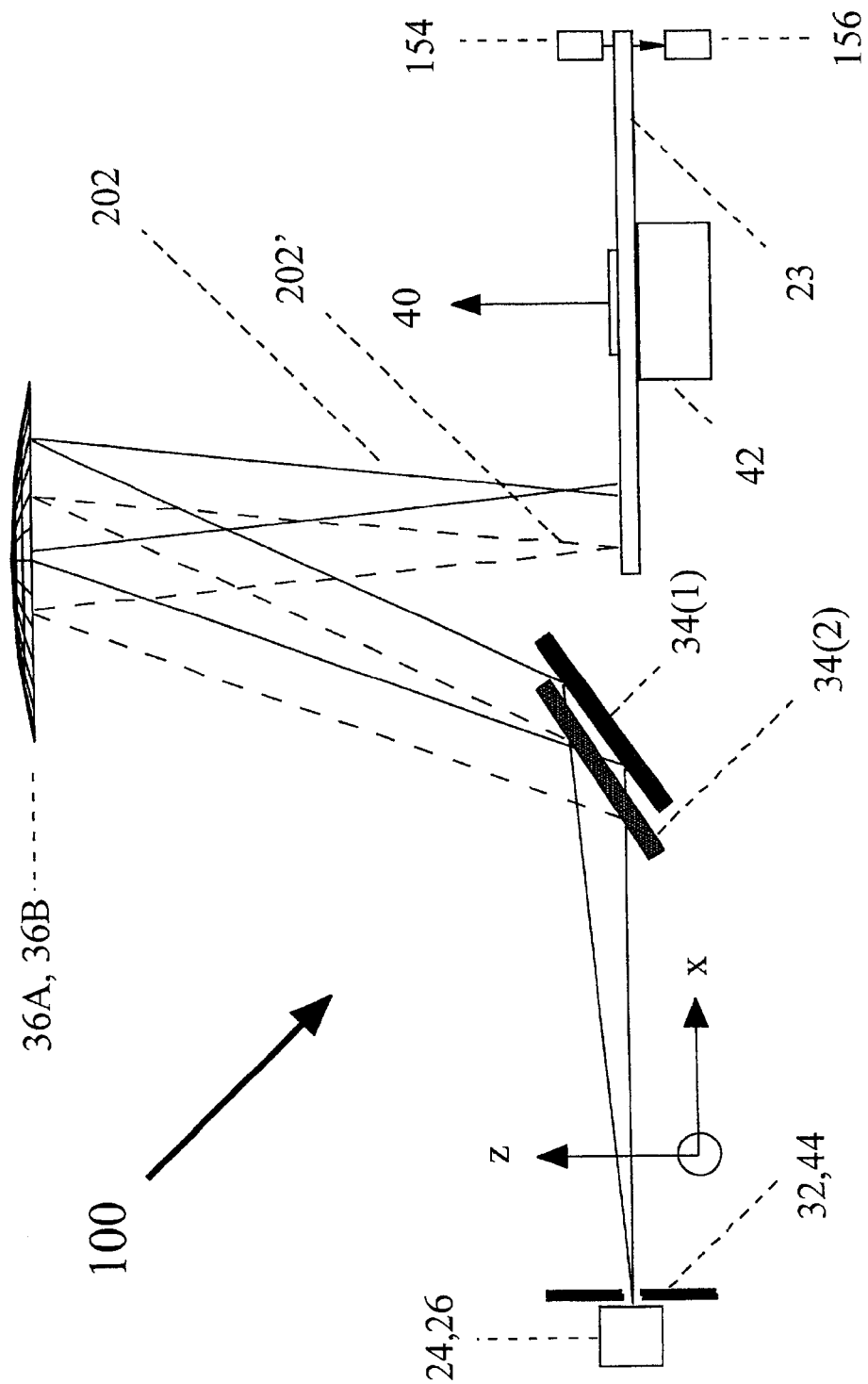
FIG. 9A is a schematic view of a spectrum analyzer that includes a folding mirror whose position is controllable to illustrate a preferred embodiment of the invention.

FIG. 9A is a schematic view of analyzer 100, depicted in FIG. 1, where the position of one or more optical elements may be controlled to correct alignment errors in the system. For brevity we define the "alignment of target image 52 onto modulator 22" to include both i) the focus of target image 52 onto the surface of substrate 23, and ii) the position of target image 52 onto modulator 22. Thus as shown in FIG. 9A, where the folding mirror 34 is in position 34(1), the input beam 202 is not properly aligned. For this purpose, the folding mirror 34 is mounted on a movable stage. Preferably, the movable stage controlled by one or more actuators driven by hardware driver 28.drv for moving the folding mirror to position 34(2), so that input beam 202' is properly focused on substrate 23 and positioned on modulator 22.

Figure 9B:
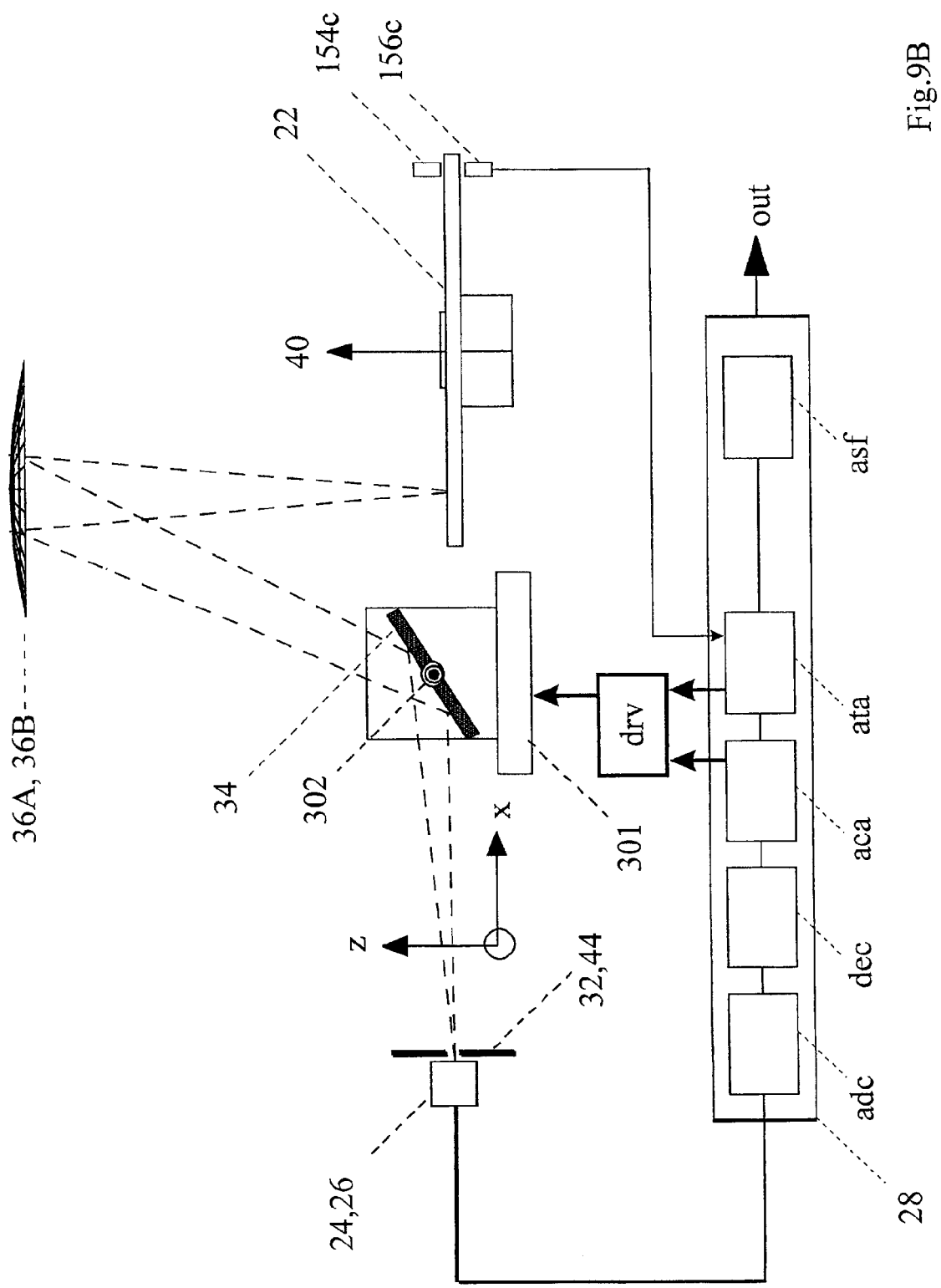
FIG. 9B is a schematic view of the spectrum analyzer of FIG. 9A, illustrating in more detail the positioning of the folding mirror, movable stage and other aspects of the analyzer.

FIG. 9B is a schematic view of analyzer 100 depicted in FIG. 1 including alignment calibration mechanism 178 and alignment tracking mechanism 179. Alignment calibration mechanism 178 is comprised of the decoded amplitudes of one or more alignment components (or channels), alignment calibration algorithm 28.aca, one or more calibration curves, hardware driver 28.drv, movable stage 301, and folding mirror 34. Alignment tracking mechanism 179 is comprised of timing/alignment marks 150, 152 and/or 153, alignment probe 79, alignment tracking algorithm 28.ata, hardware driver 28.drv, movable stage 301, and folding mirror 34. Preferably, folding mirror 34 is mounted on moveable stage 301 which incorporates one or more actuators to position folding mirror 34 to properly align target image 52 onto modulator 22.

The input for alignment tracking algorithm 28.ata is the output of alignment probe 79 in response to timing/location marks 150, 152, and/or 153 and the rotation of modulator 22. The alignment tracking algorithm 28.ata analyzes the output of alignment probe 79 to detect spindle wobble, vibration or a misaligned modulator 22 on substrate 23. Preferably, alignment tracking algorithm 28.ata generates (or calculates) one or more tracking coefficients which are then used by application specific function 28.asf to compensate for the detected spindle wobble, vibration or a misaligned modulator 22 on substrate 23. Most preferably, alignment tracking algorithm 28.ata generates a control signal for hardware driver 28.drv to manipulate one or more actuators to dynamically position one or more optical elements to keep target image 52 properly aligned. The output of the alignment tracking algorithm 28.ata can also be used to provide feedback to an assembly technician during the manufacturing process.

Figure 9C:
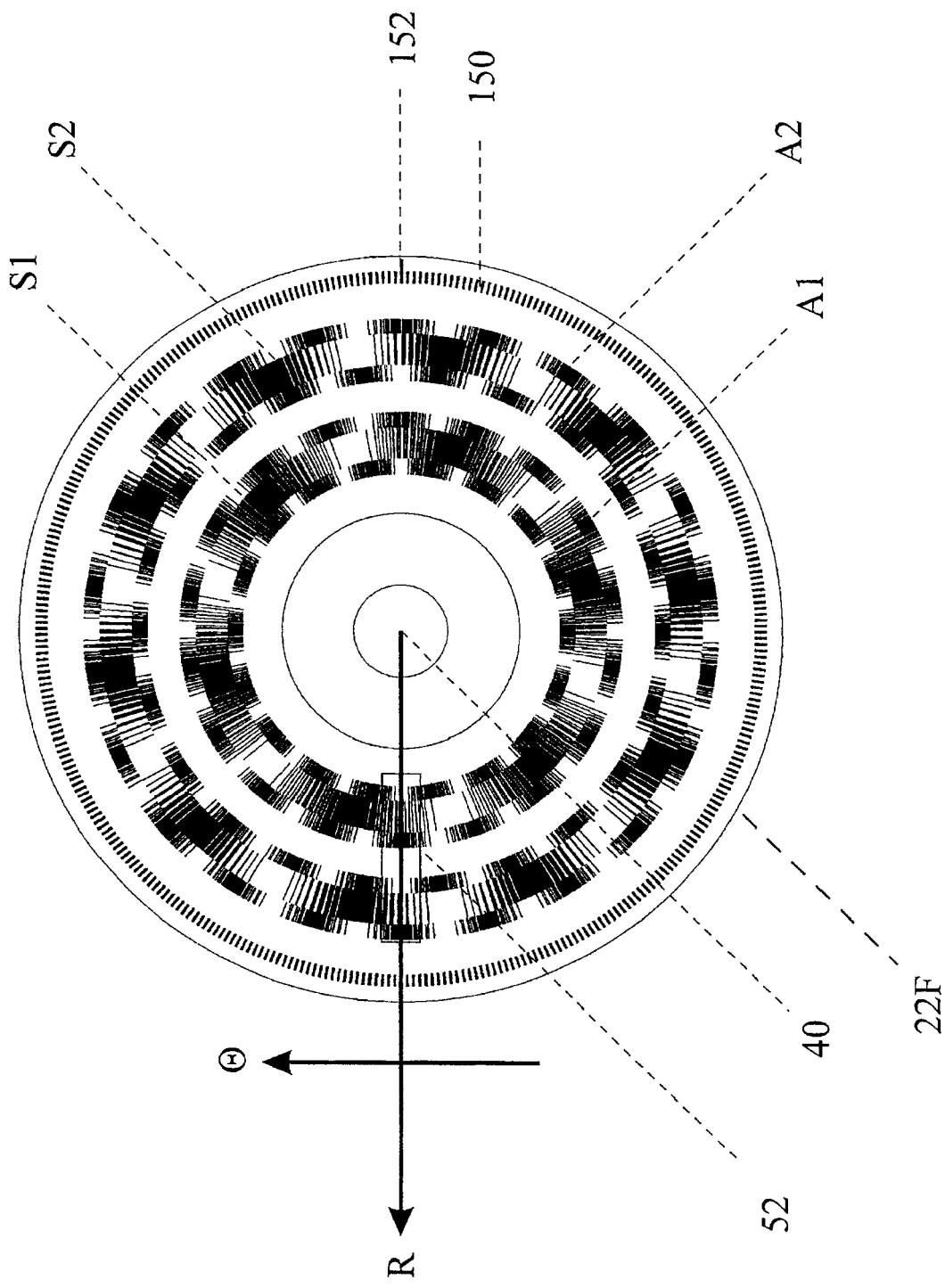
FIG. 9C is a top view of a radiation modulator useful for the embodiment of FIG. 9B.

The input for alignment calibration algorithm 28.aca is the decoded amplitudes of one or more alignment channels (or components). Dedicated filters and pairs of complementary filters organized into one or more alignment channels can be used in the analyzer depicted in FIG. 9 for alignment purposes. FIG. 9C illustrates one possible embodiment of modulator 22 with radiation filters and filter pairs comprising two signal channels and two alignment channels. In modulator 22F, the radial position of radiation filter S1 and S2 correspond to the nominal radial position of two expected alignment components in target image 52. Examples of alignment components include: the sub-images of two or more discrete fluorescent samples, dedicated reference fibers in an optical fiber array, dispersed or filtered spectral features of a sample, and dispersed or filtered spectral features in one or more optical elements (e.g., the edge of a filter). Radiation filters S1 and S2 are bounded by radiation filter pairs A1 and A2, respectively. Radiation filter pairs A1 and A2 are each comprised of radiation filters with complementary or out of phase modulation functions so that the amplitude and phase of the resulting encoded alignment component is determined by the relative proportion of radiation incident on the two filters. Preferably, the position and radial width of the filters comprising A1 and A2 are engineered to produce a characteristic amplitude and phase in the two encoded alignment components when target image 52 is properly aligned on modulator 22F. Most preferably, when target image 52 is properly aligned the intensity distributions across A1 and A2 zeros the amplitude of the encoded alignment components. Any error in the alignment of target image 52 would result in a characteristic amplitude and phase in one or more of the encoded alignment components. In this manner, a the signals in A1 and A2 provide calibration data on the magnitude and direction of the focus error and position error of target image 52 on substrate 23 and modulator 22F, respectively. Preferably, one or more calibration curves are generated by precisely detuning the focus and position of target image 52 onto substrate 23 and modulator 22F, respectively, (e.g., using hardware driver 28.drv and movable stage 301) and recording the resulting amplitude and phase of the encoded alignment components. More preferably, alignment calibration algorithm 28.aca inputs the amplitudes and phases of the current alignment components and uses the calibration curves to generate one or more calibration coefficients which are then used by application specific function 28.asf to compensate for the effects of the alignment error. Most preferably, alignment calibration algorithm 28.aca compares the current alignment to the calibration curves to generate a control signal for hardware driver 28.drv to manipulate one or more actuators to position one or more optical elements to keep target image 52 properly aligned. The output of the alignment calibration algorithm 28.aca can also be used to provide feedback to an assembly technician during the manufacturing process. A proper alignment of target image 52 along the azimuthal axis of modulator 22 can be obtained by simply maximizing the amplitude of the encoded components resulting from S1 and S2.

The shared components of alignment calibration mechanism 178 and alignment tracking mechanism 179 shown in FIG. 9B were chosen for illustrative purposes and are not meant to limit the scope of the invention. Other configurations which utilize independent (or multiple independent) input sources, hardware drivers, movable stages, actuators, and optical components are within the scope of the invention. In the preceding description, folding mirror 34 was chosen for illustrative purposes, it being understood that the position of other optical elements, including various combinations of entrance aperture 32, exit aperture 44, pre-encoder optic 36A, post-encoder optic 36B, detector 26, and modulator 22, could be controlled for alignment purposes, and are within the scope of the invention. The radiation filters used in modulator 22F were chosen for illustrative purposes, it being understood that other filter pair and filter combinations are useful for alignment purposes and are within the scope of the invention. In particular, various aspects of the modulators 22D and 22E shown in FIG. 7 and FIG. 8, respectively are useful for alignment purposes. The calibration and alignment mechanisms described above are applicable to all of the embodiments of the present invention.

Interlaced Excitation Anlyzer 300

In some applications, it may be desirable to measure a samples response to two or more different components of excitation radiation. Examples of components of excitation radiation include a collection of different lasers, a multi-line laser or low-pressure gas lamp combined with a diffractive or refractive optic to separate the emission lines, optical fibers, or lamp/filter combinations. Examples of samples include a multi-lane/multi-capillary electrophoresis, and a collection of distinct fluorescence emitting (or Raman scattering) samples arranged in a linear array. Such and other examples of excitation components and samples are within the scope of the invention. In some instances, it may also be desirable to measure a samples response to two or more different excitation components substantially simultaneously. For example, some samples are altered by the excitation radiation such that the results of a sequence of excitation/response measurements may differ depending upon the order of the applied excitation components. Another example is a sample which is flowing in a process stream (e.g., electrophoresis) where the dwell time at the location of the measurement is insufficient to make the excitation measurements in series. The interlaced excitation analyzer described below, and shown in FIG. 10, permits the emitted, scattered, transmitted or reflected radiation from a sample in response to two or more different excitation components to be detected substantially simultaneously.

Figure 10A:
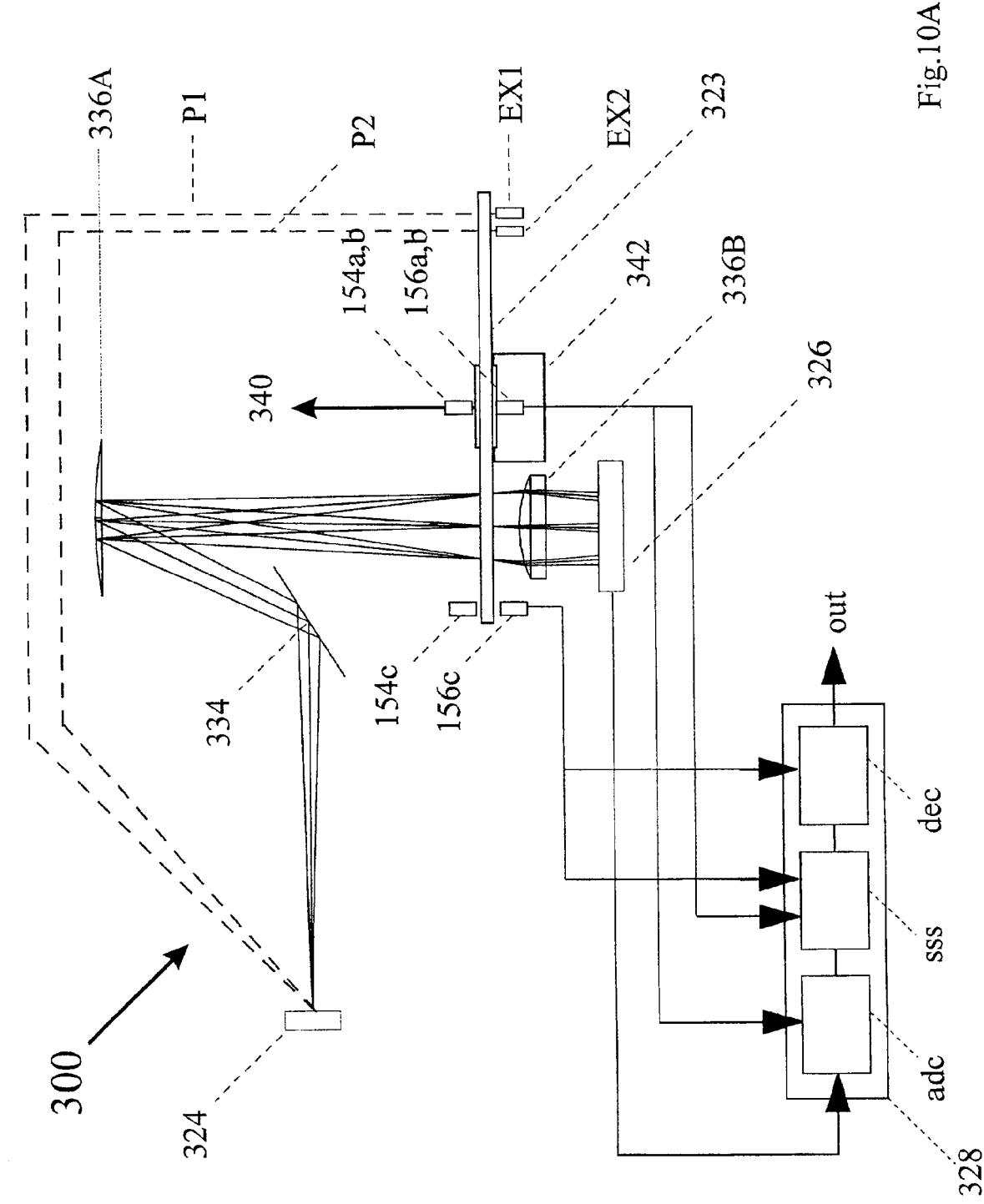
FIG. 10A is a schematic view of a spectrum analyzer useful for measuring the optical characteristics of a sample when excited by means of two distinct excitation sources.

FIG. 10A is a schematic view of analyzer 300, which is based on analyzer 100 of FIG. 1 and includes an interlacing mechanism to excite a radiation emitting sample with two or more distinct components of excitation radiation substantially simultaneously. In FIG. 10A, one or more excitation sources (not shown) provides excitation radiation comprised of two distinct excitation components, EX1 and EX2. In analyzer 300, excitation components EX1 and EX2 are directed to sample 324 substantially in sequence (e.g., interlaced) along optical paths P1 and P2 as modulator 322 is rotated about rotation axis 340. Preferably, the excitation sequence substantially precludes more than one of the excitation components from reaching the sample 324 at any given time. Preferably, a variable attenuator may be used to precondition or preset the intensities of the excitation components. In response to the encoded excitation beam, sample 324 emits, transmits, reflects or scatters a response beam of radiation, which is comprised of at least two response components. The response beam is imaged by pre-encoder optic 336A to form a target image 352 with response components focused at substantially different points along the radial axis on modulator 322. Modulator 322 has at least two radiation filters at different radii from the rotation axis 340 for encoding the response components to provide an encoded response beam. Preferably, target image 352 is aligned with the radiation filters such that the encoded components have a substantially one to one correspondence with the response components. Preferably, the amplitudes of the encoded response components are substantially smooth functions or change between three or more substantially distinct levels of contrast as modulator 322 is rotated about the rotation axis 340. More preferably, the amplitudes of the encoded response components are substantially orthogonal to one another. Most preferably, the amplitudes of the encoded response components are all digitized approximations of the general form $\sin^2(m\theta+p\pi/4)$. The encoded response beam is collected, directed and focused by post-encoder optic 336B onto detector 326. In response to the encoded response beam, detector 326 provides an output to the analog-to-digital converter (ADC) 328.adc on computer 328. As shown in FIG. 10A, Computer 328 (which includes all the features of computer 28) includes a sub-signal separator algorithm 328.sss which separates the time-based signal generated by detector 326 in response to the encoded response beam into two sub-signals which correspond to the encoded response beam resulting from EX1 or EX2, respectively. The sub-signals are then independently analyzed by decoding algorithm 328.dec to provide the amplitudes of the encoded response as a function of the excitation components.

If sample 324 is a single sample with a plurality of selected response components, analyzer 300 allows one to measure substantially the selected response components as a function of the excitation components substantially simultaneously. If sample 324 is a collection of samples and the response components are spatial components which also contain spectral information of interest (e.g., a multi-lane, multi-dye electrophoresis or multi-dye fluorescent assay), the spectral properties of the response components can be determined by inserting a spectrometer or other wavelength filtering device between optical element 336B and detector 326 and scanning the wavelength of the radiation transmitted to detector 326. More preferably, a spectrograph or other wavelength separating device is used to direct a number of selected spectral components of the encoded beam to an equal number of detectors. Most preferably, computer 328 would include a sufficient number of analog-to-digital converters (ADCs) and decoding algorithms 328.dec such that the signals generated by the detectors in response to the encoded beam could be analyzed substantially simultaneously.

Figure 10B:
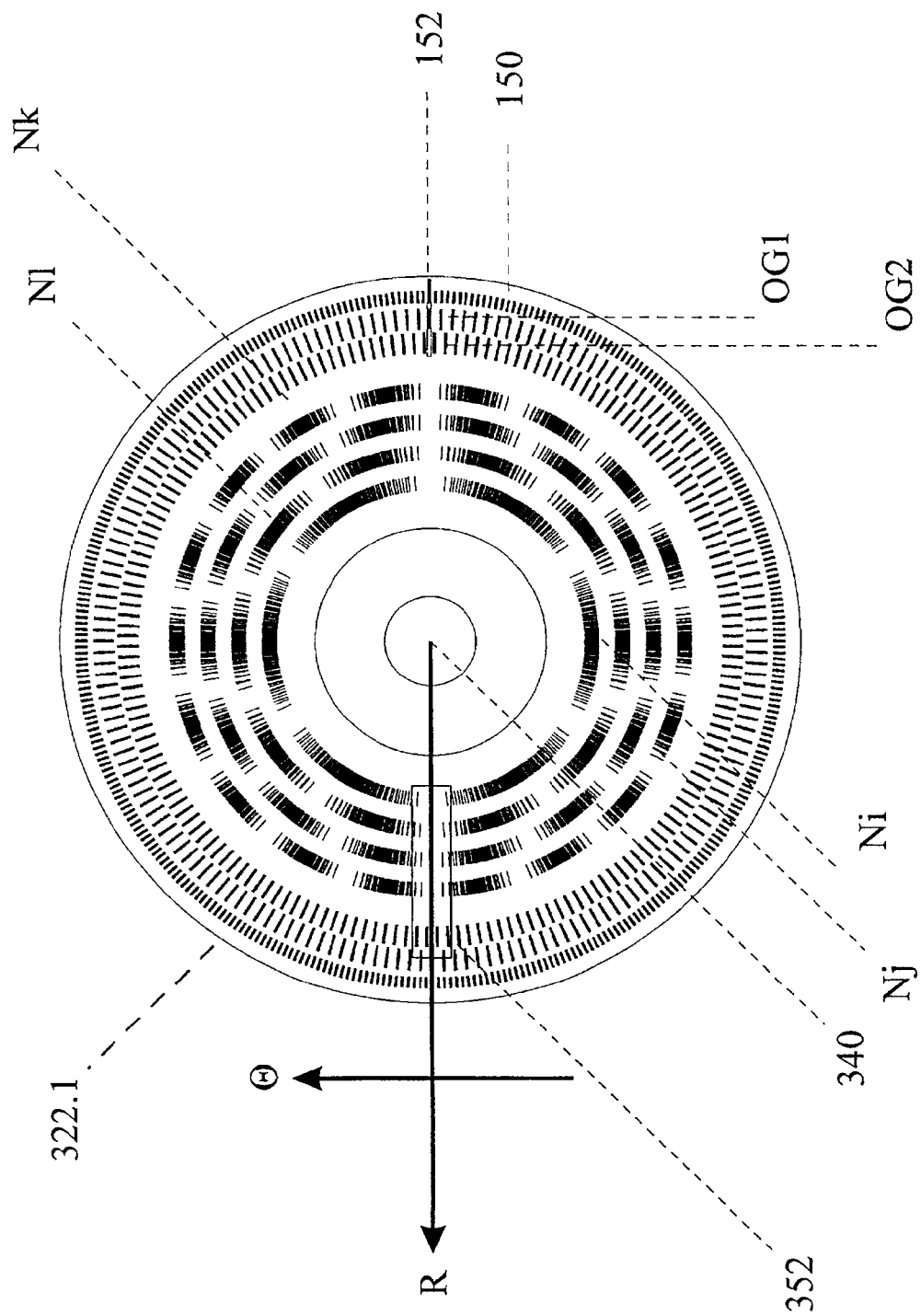
FIG. 10B is a top view of a spatial radiation modulator useful for the embodiment of FIG. 10A.

FIG. 10B illustrates one possible embodiment of modulator 322 a for use with analyzer 300. Modulator 322.1 includes a series of staggered optical gates OG1 and OG2 centered at R1 and R2, respectively. OG1 and OG2 alternately permit the transmission of radiation components EX1 or EX2, such that radiation from only one of the excitation components is incident on the sample 324 at any given time. Preferably, the staggered optical gates have the same resolution as timing marks 150, where every other gate is open, and the relative phase of the open gates in the two annular regions are such that only one gate is open at a time. The gates may simply be transmissive areas in an opaque substrate or reflective areas in a non-reflective or transparent substrate. The response beam of radiation is collected and focused to form a target image 352 substantially along a radial axis of modulator 322.1 such that the response components are focused at substantially different points along the radial axis of modulator 322.1. The response components are encoded by the four spatial radiation filters, Ni, Nj, Nk and Nl, on modulator 322.1 to provide an encoded response beam. Preferably, each of the modulation functions of 322.1 used to encode the response beam is a smooth function or a digitized replica of a smooth function having three or more distinct levels of contrast as modulator 322.1 is rotated about rotation axis 340. More preferably, the amplitudes of the encoded response components are substantially orthogonal to one another. Most preferably, the encoded response components are modulated substantially according to functions of the form $\sin^2(m\theta+p\pi/4)$.

In FIG. 10A and FIG. 10B, the optical geometry and the number of excitation components and encoding radiation filters was chosen for clarity, it being understood that arbitrary numbers of excitation components and radiation filters are within the scope of the invention. Other optical geometries which involve separate, more elaborate optical elements or optical system to collect and focus the input radiation onto modulator 322 and to collect and focus the encoded beam from modulator 322 onto detector 326 may be used instead in each of the embodiments herein and such variations are within the scope of the invention. The transmission mode of modulator 322 was chosen for clarity, it being understood that a similar device with a reflective modulator is within the scope of the invention.

In FIG. 10A and FIG. 10B, staggered optical gates, OG1 and OG2, of modulator 322.1 are used to direct the excitation components to sample 324 in an interlaced sequence. This interlacing mechanism could be replaced with by an interlaced sequence of control signals (not shown) from computer 328 to one or more controllable gating devices which direct the excitation components to 324. Examples of controllable gating devices include addressable optical shutters, movable mirrors and controllable power supplies. In this case, computer 328 would produce a sequence of control signals to a number of controllable gating sources in response to one or more optical switches (e.g., optical switch 77) to direct the excitation components to sample 324 substantially in sequence.

In reference to FIG. 9, for analyzer 300 described above, the position one or more optical elements can be controlled to align target image 352 onto modulator 322. Preferably, sample 324 includes a number of alignment components (e.g., one or more known fluorescent species, one or more light-emitting diodes, or one or more optical fibers with know spectral output distributed at known spatial positions within 324) and modulator 322 includes a number of alignment channels to provide input to the alignment calibration algorithm 28.aca. Preferably, calibration algorithm 28.aca generates one or more calibration coefficients which are then used by application specific function 328.asf to compensate for the effects of the alignment error. More preferably, calibration algorithm 328.aca generates a control signal for hardware driver 28.drv to position one or more optical elements to properly align target image 352 onto modulator 322. More preferably, the alignment spatial components would also have known spectral excitation/emission properties for calibrating the wavelength filtering device or the wavelength separating device.

Harmonics of Incomplete Rotation Periods

The encoding functions used in modulators 22A–22D are harmonics of the complete rotational period of substrate 23. In other embodiments, harmonics of incomplete rotational periods may be useful for eliminating various hardware items, freeing up micro-processor resources, synchronizing the movements of external mechanical devices, measuring the position and intensity of an intensity distribution, and increasing the spatial or spectral resolution of the analyzer. Modulator 22E of FIG. 8 is an example of using modulation functions based on two incomplete rotation periods to measure both the intensity and radial position of an imaged radiation distribution, thereby enhancing the measurement capability of analyzer 100.

Figure 11A:
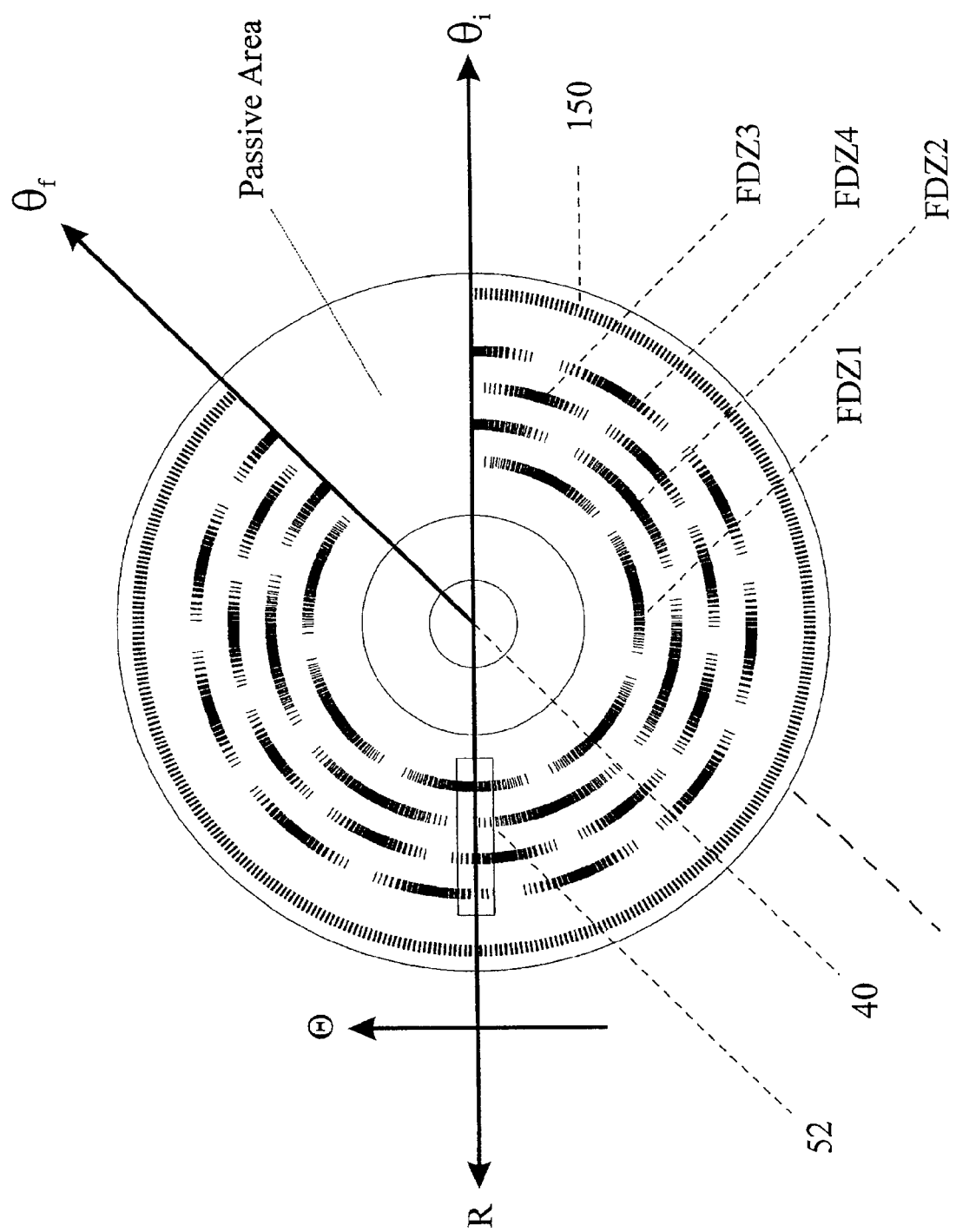
FIG. 11A is a top view of radiation modulator which incorporates radiation filters which are based on harmonics of an incomplete rotational period.

In another embodiment of modulator 22, harmonics of an incomplete rotation period may be used to eliminate timing mark(s) 152 on modulator 22 and optical switch 78 by replacing the signal from optical switch 78 with a simple time-out on the signal originating from optical switch 77. FIG. 11A is a top view of radiation modulator which incorporates radiation filters which are based on harmonics of an incomplete rotational period. As shown in FIG. 11, radiation modulator 22DZ has four radiation filters, FDZ1–FDZ4, which are harmonics of the incomplete rotation period which starts at the rotation angle $\theta i$ and ends at the rotation angle $\theta f$. Between $\theta f$ and $\theta i$, modulator 22DZ includes a passive area which is void of the radiation filters. For clarity, we define the active period as the fraction of a complete rotation period where target image 52 is being modulated by the radiation filters on modulator 22, and we define the passive period as the fraction of a complete rotation period where target image 52 is not being modulated by the radiation filters on modulator 22. Preferably, the timing marks 150 on modulator 22DZ are patterned such that during the passive period no ADC trigger events are generated by optical switch 77. To use modulator 22DZ, the decoding algorithm 28.dec of radiation analyzer 100 would be modified to eliminate the input from optical switch 78 and include a timer which would provide a basis for measuring the elapsed time between ADC trigger events generated by optical switch 77 in response to timing marks 150. The elapsed time between ADC trigger events would be used to compute an average ADC trigger event period. Decoding algorithm 28.dec would include an function which would generate an ADC time-out event when the time elapsed since the last ADC trigger event is substantially greater than the average ADC trigger event period. Preferably, modulator 22DZ is patterned such that the ADC time-out event occurs during the passive period. The ADC time-out event is used by computer 28 to synchronize decoding algorithm 28.dec with the output from 28.adc. In this manner, the cost and complexity of radiation analyzer 100 is substantially reduced.

Harmonics of an incomplete rotation period in conjunction with a passive period may also be necessary when a computer-time-intensive algorithm is executed once per rotation period and would otherwise compromise the data collection and decoding efforts. For example, in analyzer 100 the data is acquired during an incomplete rotation period and the application-specific algorithm 28.asf is executed during the passive period. In this manner, 28.asf can be executed every rotation period without having to skip data acquisition cycles.

Harmonics of an incomplete rotational period in conjunction with a passive period may also be useful in applications where one or more optical elements are re-positioned every rotational period of modulator 22. For example, analyzer 100 is configured to measure the spatial components of an extended source and a spectrometer is inserted before detector 26 to isolate a specific spectral component of the spatially-encoded signal. The spectrometer grating is stepped once per rotation period to the next wavelength during the passive period. Preferably, the passive period is long enough such that any residual motion of the optical element(s) is damped to an acceptable level prior to re-starting the DAQ. In this manner, the spectral properties of each spatial component can be mapped out over a small number of rotation periods. Another example is where analyzer 100 is configured to measure the spectral components of an extended source and a mirror or other optical element is mounted on a movable stage to isolate specific portions of the extended source along one or more spatial axis. The movable stage is stepped once per rotation period during the passive period. In this manner, the spatial and spectral properties of an extended source can be mapped out over a small number of rotation periods. Another example is where analyzer 100 is configured to measure the spatial components of a two-dimensional extended source along a first spatial axis and a mirror or other optical element is mounted on a movable stage to isolate specific cross sections of the extended source along a second spatial axis. The movable stage is stepped once per rotation period to the isolate the next specific cross section of the extended source during the passive period. In this manner, a two-dimensional image of the extended source can be obtained over a small number of rotation periods.

Figure 11B:
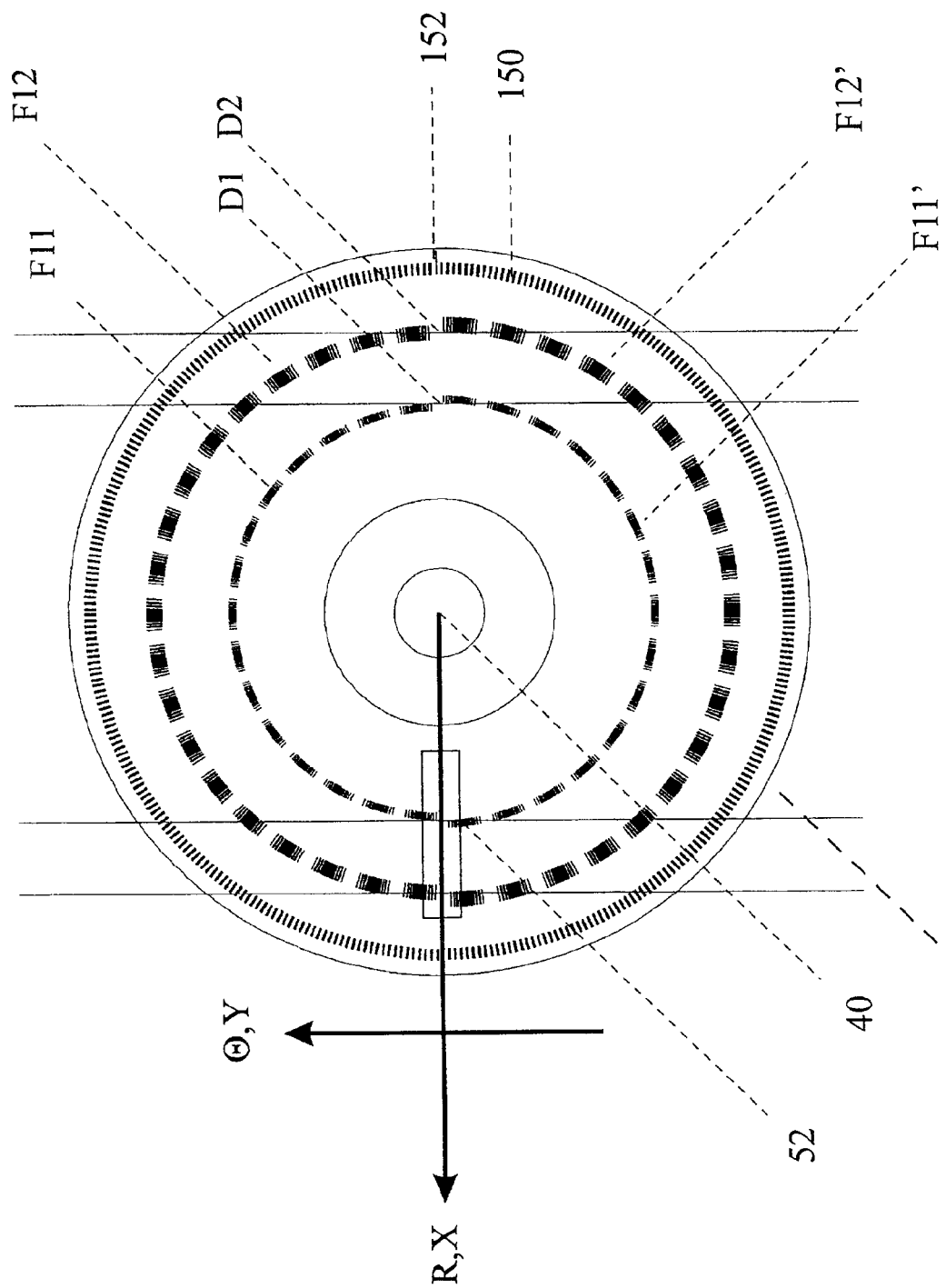
FIG. 11B is a top view of a radiation modulator illustrating two methods to increase the spatial resolution of the encoding of target image 52.

In another embodiment of analyzer 100, harmonics of two or more incomplete rotation periods may be combined to increase the number of encoding channels without increasing the number of harmonics in the encoded beam. In this manner, the total modulation bandwidth of the encoded beam, and thereby the bandwidth of the signal generated by detector 26, can be minimized. FIG. 11B illustrates two methods to increase the spatial resolution of the encoding of target image 52. Modulator 22G is comprised of two set of radiation filters which are harmonics of incomplete rotational periods. Radiation filters F11 and F12 are harmonics of the first half of the rotation period, and radiation filters F11' and F12' are harmonics of the second half of the rotation period. Radiation filters F11 and F11' (F12 and F12') have the same phase and frequency. In addition, radiation filters F11 and F11' (F12 and F12') have the same radial width. As seen along line in FIG. 11B, radiation filter F11' is displaced along the radial axis with respect to radiation filter F11 by a distance greater than or equal to the radial width, and radiation filter F12' is displaced along the radial axis with respect to radiation filter F12 by a distance less than the radial width. As such, the total number of distinct encoding channels is four and the total number of distinct encoding frequencies and phases is two. To use modulator 22G, the sub-signal separator 28.sss of radiation analyzer 100 would separate the encoded signal into two sub-signals, ES1 and ES2, corresponding to the first half and the second half of the rotation period of modulator 22G, respectively. ES1 would be processed by decoding algorithm 28.dec to yield the amplitudes of the components encoded by F11 and F12, and ES2 would be processed by decoding algorithm 28.dec to yield the amplitudes of the components encoded by F11' and F12'. In this manner, four radial sections of target image 52 can be determined using two encoding functions.

In the preceding discussion, the number of incomplete rotation periods and passive periods, the number of filters in each incomplete rotation period, and the radial displacements from one incomplete rotation period to another were chosen for clarity and are not meant to limit the scope of the invention.

Hyper-Spectral Imaging Anlyzer 500

In some applications, it is necessary to measure a number of spectral components of a limited collection of discrete radiation emitting samples. Examples of collections of radiation emitting samples include multi-dye, multi-capillary (or multi-lane) electrophoresis, multi-dye, multi-sample fluorescent assay, and a linear array of optical fibers containing spectral components from a remote sampling location. Typically, a CCD camera in conjunction with optics that project spatial information along a first axis and spectral information along a second axis are used for this purpose. Significant advantages in cost and performance can be realized if the CCD camera is replaced by a single photo-multiplier tube (PMT) and a multi-channel optical encoder.

Another embodiment of analyzer 100 depicted in FIG. 1, is a multi-channel, spectrum analyzer (analyzer 500), designed to measure a plurality of spectral components individually selected from two or more radiation emitting samples substantially simultaneously. Radiation source 524 is a collection of two or more radiation emitting samples, each said sample emitting radiation in a plurality of selected spectral components. Radiation emitted by source 524 is imaged by pre-encoder optic 536A (a one-dimensional hyper-spectral imaging optic), to form target image 552 on modulator 522. Target image 552 is comprised of a plurality of spectral components (individually selected from each of the radiation emitting samples), substantially separated from one another along a common radial axis of modulator 522. Modulator 522 includes a number of radiation filters to encode target image 552 to provide an encoded beam comprising two or more encoded components. Preferably, target image 552 is aligned with said radiation filters such that said encoded components have a substantially one to one correspondence with said selected spectral components. The encoded beam is collected, directed and focused with post-encoder optic 536B onto detector 526. Computer 528 (which includes all the features of computer 28) then analyzes the signal generated by detector 526 in response to the encoded beam to determine the amplitudes of the encoded components.

FIG. 12A is a schematic of one embodiment of pre-encoder optic 536A, used to project spectral components the of two radiation emitting samples along a common encoding axis. As shown in FIG. 12A, pre-encoder optic 536A.1 is comprised of two collection lenses, 536A.C.1 and 536A.C.2, a single diffraction grating 536A.DG, and two focusing lenses, 536A.F.1 and 536A.F.2. The two collection lenses are positioned along a substantially common collection axis, $Y_c$. The collection lenses are positioned to collimate radiation emitted from two radiation emitting samples, 524.1 and 524.2, arrayed along a substantially common sample axis, $Y_s$. The collimated radiation beams are diffracted by diffraction grating 536A.DG, and focused by focusing lenses 536A.F.1 and 536A.F.2 (arrayed along a substantially common focusing axis, $Y_f$), to form two dispersed images substantially in a common encoding plane and with the respective dispersion axes substantially along a common encoding axis, $Y_e$. Using pre-encoder optic 536A.1, target image 552 is comprised of two dispersed images, 552.1 and 552.2, corresponding to radiation emitting samples 524.1 and 524.2, with the respective dispersion axes substantially separated from one another along encoding axis $Y_e$. As shown in FIG. 12A, the plane of diffraction grating 536A.DG is tilted and the positions of focusing lenses 536A.F.1 and 536A.F.2 are engineered (e.g., displaced along the Y axis relative to the collection lenses) to direct zeroth-order, non-diffracted radiation out of the preferred beam path. Preferably, pre-encoder optic 536A incorporates one or more bandpass filters 536.BPF to prevent the two dispersed images from overlapping one another. If the samples comprising 524 are excited with excitation radiation, it is preferable that the bandpass filter has finite transmission at the wavelength(s) of the excitation radiation such that the sub-image of the excitation radiation can be used for alignment purposes. In the present invention, pre-encoder optic 536A is to be used with modulator 522. However, pre-encoder optic 536A can also be used with a linear detector array, a scanning aperture, or an addressable spatial light modulator. These and other applications of pre-encoder optic 536A are within the scope of the invention.

Figure 12B:
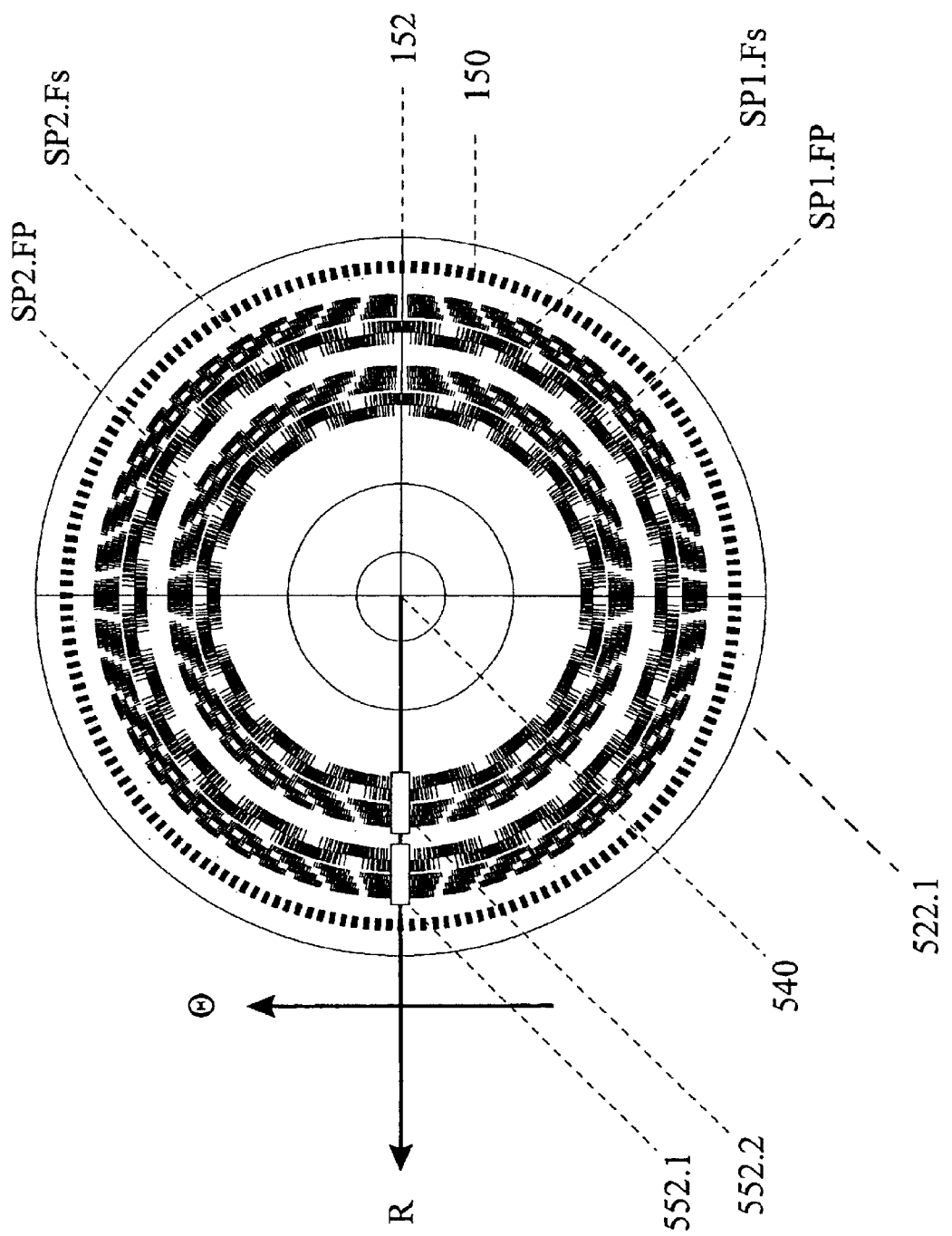
FIG. 12B is a top view of one embodiment of modulator 22 to be used with a one-dimensional hyper-spectral pre-encoder optic.

FIG. 12B is a schematic of one embodiment of modulator 522 to be used in analyzer 500 with pre-encoder optic 536A.1. Modulator 522.1 includes two sub-patterns, SP1 and SP2, for encoding the dispersed images of the two radiation emitting samples. Each sub-pattern includes a number of radiation filters, SP1.Fs and SP2.Fs, for measuring selected spectral components from each sample. In addition, each sub-pattern includes a complementary filter pair, SP1.FP and SP2.FP, positioned at the expected (or anticipated) radial position for an alignment spectral component (expected in each radiation emitting sample) for calibration and alignment purposes. Examples of alignment components include scattered excitation energy, Raman lines, and spectral features in one or more optical elements. Preferably, the signals from the two filter pairs are used by computer 528 to calibrate the alignment of target image 552 on modulator 522A. More preferably, the signals from the two filter pairs are used as input for the alignment calibration algorithm 528.aca, which in turn, generates a control signal for hardware driver 528.drv to position one or more optical elements to align target image 552 onto modulator 522A.

In analyzer 500 there are two obvious competing encoding strategies: 1) separating the sub-images to obtain higher signal levels at the expense of spectral resolution, or 2) interlacing the sub-images to obtain higher spectral resolution at the expense of signal level. If higher spectral resolution is needed, a multi-band-pass filter can be inserted between source 524 and detector 526, thereby allowing the dispersed sub-images to be interlaced with a substantial increase in spectral resolution. However, this increased spectral resolution comes at the expense of signal level which is reduced by the multi-band-pass filter.

In FIG. 12A and FIG. 12B, the optical geometry and the number of radiation emitting samples, optical components, and encoding radiation filters (and filter pairs) was chosen for clarity, it being understood that arbitrary numbers of radiation emitting samples, optical components, radiation filters, and complementary filter pairs are within the scope of the invention.

EXAMPLES

The present invention will be further described by the following examples. These examples are intended to embody the invention but not to limit its scope. In all of the examples described below, it is preferred that each of the modulation functions are smooth functions or digitized replicas of smooth functions having three or more distinct levels of contrast as the spatial radiation modulator is rotated about rotation axis 40. Most preferably, the modulation functions are of the form $\sin^2(m\theta+p\pi/4)$. In the descriptions that follow we shall use the following nomenclature for the core components of analyzer 100, analyzer 300, and analyzer 500 which are modified specifically for the given example:

Component.Example.Multiplicity

Where the MULTIPLICITY is used in examples where more than one instance of a given component (or a distinction between sub-components) is required for a given application. Additional components required by the examples will be given unique symbols.

Example 1

The first example of the dual-use analyzer 100 depicted in FIG. 1, analyzer 100.1, is a multi-spectral-component encoded source with a high-intensity, collimated beam which can be used to excite radiation emitting samples, or to measure absorbing gasses and vapors over a large distance, or to probe optically dense media such as liquids or solids. Radiation source 24.1 is a collimated radiation beam having a plurality of selected spectral components (e.g., an argon-ion or a carbon dioxide laser). Pre-encoder optic 36A.1 includes a diffractive or refractive element to separate the selected spectral components to form a target image along a radial axis of modulator 22.1. Preferably, pre-encoder optic 36A.1 includes a variable attenuator to precondition or preset the intensities of the selected components. Target image 52.1 is a dispersed image comprised of selected spectral components focused at substantially different points along said radial axis of modulator 22.1. Modulator 22.1 includes a number of radiation filters which encode the selected spectral components to provide an encoded beam comprised of a plurality of encoded spectral components as modulator 22.1 is rotated about rotation axis 40. Preferably, target image 52.1 is aligned with the radiation filters such that the encoded components have a substantially one to one correspondence with the selected spectral components. Preferably, post-encoder optic 36B.1 includes a diffractive or refractive element to substantially collimate the encoded components. In this manner, the encoded beam can be propagated over a long distance to a remote sampling station and measured with a remote detector RD26 (similar to detector 26). Preferably, the signals generated by RD26 in response to the encoded beam are sent back to analyzer 100.1 for analysis by computer 28, which determines the amplitudes of the encoded components. More preferably, the encoded beam is split up with a beam splitter and distributed to a number of remote sampling stations along with the timing and alignment signals generated by optical switches 77 and 78, and alignment probe 79, in response to the rotation of modulator 22.1. Most preferably, the collimated, encoded beam is launched into an optical fiber, waveguide, light pipe or purged (or evacuated) tubing and distributed to the remote sampling stations such that the uncontrolled path of the encoded beam is substantially limited outside of the remote sampling (or excitation) station. Preferably, each of the remote sampling stations include at least one remote detector RD26 and a remote computer RC28 (with the same decoding functionality as computer 28) for analyzing the signals generated by the detector and the timing and alignment signals. In this manner, the data acquired at the remote locations can be properly analyzed.

In reference to FIG. 9, for the analyzer described above, the position of one or more optical element can be controlled by hardware driver 28.drv to align target image 52.1 onto modulator 22.1. Preferably, one or more spectral components in source 24.1 are analyzed to provide input to the alignment calibration algorithm 28.aca, which in turn, generates a control signal for hardware driver 28.drv to position one or more optical elements to properly align target image 52.1 onto modulator 22.1.

Example 2

The second example of the dual-use analyzer 100 depicted in FIG. 1, analyzer 100.2, is compact spectrum analyzer which uses a collection of bandpass filters or a linear variable filter (LVF) to provide a plurality of selected radiation components. In analyzer 100.2, the radiation source is comprised of a broad band or multi-wavelength source filtered by a linear array of two or more bandpass filters or a linear variable filter (LVF). Taken together the radiation source and the collection of bandpass filters or LVF comprise extended source 24.2, having a number of spatial components corresponding to the radiation transmitted through (or reflected from) the individual bandpass filters or specific positions along the LVF. The radiation filtered by the array of bandpass filters or LVF is imaged by pre-encoder optic 36A.2 to form target image 52.2 substantially along a radial axis of modulator 22.2. Target image 52.2 is comprised of the sub-images of the radiation transmitted through (or reflected from) the collection of different bandpass filters or selected portions of LVF focused at substantially different points along said radial axis of modulator 22.2. Modulator 22.2 has a number of radiation filters at different radii for encoding the spatial components to provide an encoded beam as modulator 22.2 is rotated about the rotation axis 40. Preferably, the spatial components are aligned with the radiation filters such that the encoded components have a substantially one to one correspondence with the radiation transmitted through the individual bandpass filters or selected portions of the LVF. The encoded beam is collected, directed and focused with post-encoder optic 36B onto detector 26. Computer 28 then analyzes the signal generated by detector 26 in response to the encoded beam to determine the amplitudes of the encoded components. A sample or sample cell can be inserted between the source 24.2 and detector 26. In this manner, the spectral properties of a sample can be measured.

In reference to FIG. 9, for the analyzer described above, the position of the collection of bandpass filters or LVF (and/or other optical elements) can be controlled by hardware driver 28.drv to align target image 52.2 onto modulator 22.2. Preferably, extended source 24.2 includes a number of alignment spatial components (e.g., a non-transmitting mask which obscures the border between individual bandpass filters or selected portions of the LVF) and modulator 22.2 includes a number of alignment channels to provide input to the alignment calibration algorithm 28.aca, which in turn, generates a control signal for hardware driver 28.drv to position one or more optical elements to align target image 52.2 onto modulator 22.2.

Example 3

The third example of the dual-use analyzer 100 depicted in FIG. 1, analyzer 100.3, is a spectrum analyzer, which is used for both analyzing and providing feedback to simultaneously control the center wavelengths of a number of tunable radiation sources. Radiation source 24.3 is comprised of a plurality of spectral components, where each spectral component corresponds to a distinct radiation source and is characterized by an intensity and a center wavelength. For example, radiation source 24.3 may be an optical fiber containing a plurality of optical signals, where each signal corresponds to a different radiation source. Radiation emitted by source 24.3 is imaged by pre-encoder optic 36A.3 to form a target image 52.3 onto modulator 22.3. Target image 52.3 is comprised of a plurality of sub-images focused at substantially different points along a radial axis of modulator 22.3, where each sub-image corresponds to a distinct radiation source. Pre-encoder optic 36A.3 is comprised of a least one diffractive element such that a change in the center wavelength of any one of the distinct radiation sources will cause the corresponding sub-image to move substantially along the radial axis of modulator 22.3. Modulator 22.3 has a number of radiation filter pairs (similar to FP1 in modulator 22D of FIG. 7) at different radii for encoding the spectral components to provide an encoded beam as modulator 22.3 is rotated about rotation axis 40.3. The radiation filter pairs are each comprised of radiation filters having modulation functions that are complementary or out of phase so that the amplitude and phase of the encoded component is determined by the relative proportion of radiation incident on the two filters. The encoded beam is collected, directed and focused by post-encoder optic 36B.3 onto detector 26.3 and computer 28.3 analyzes the signals generated by the detector in response to the encoded beam. Computer 28.3 computes the amplitudes and phases of the encoded components from the signals generated by detector 26.3 in response to the encoded beam. Preferably, computer 28.3 generates a number of distinct control signals for adjusting the center wavelengths of the distinct radiation sources in response to the signals generated by detector 26.3 to tune the sources. Preferably, the radiation filters comprising each pair are substantially adjacent to one another, and the border between the adjacent radiation filters is substantially located at the radius which correspond to the radial position of a corresponding sub-image for the nominal or desired center wavelength for the corresponding tunable radiation source. In this manner, the amplitudes of the encoded components are zeroed (or nulled) when the center wavelengths of the radiation sources are tuned to the nominal or desired center wavelengths. Any deviation of a given tunable source from the preferred configuration results in a signal (in its corresponding modulation channel) in which the sign and amplitude of the decoded signal indicates the direction and magnitude of the displacement of the center wavelength, respectively. In such manner, the decoded signal can be used as a feedback mechanism to preserve the tunable sources in the optimum configuration. Thus, where temperature or other environmental changes cause the center wavelength to drift, the decoded signal may be used for tuning the tunable radiation source in order to maintain a stable and constant center wavelength, such as by changing the temperature or current of the source.

In reference to FIG. 9, for the analyzer described above, the position of one or more optical elements can be controlled by hardware driver 28.3.drv to align target image 52.3 onto modulator 22.3. Preferably, source 24.3 includes a number of alignment spectral components (e.g., a reference laser or a number of lines of a gas or impurity spectrum) and modulator 22.3 includes a number of alignment channels to provide input to the alignment calibration algorithm 28.3.aca, which in turn, generates a control signal for hardware driver 28.3.drv to position one or more optical elements to align target image 52.3 onto modulator 22.3.

Preferably, the intensities of the distinct radiation sources are measured from time to time. For this purpose, hardware driver 28.3.drv can be used to reposition one or more optical elements to move target image 52.3 along the radial axis from its default position to a detuned position. This in turn collectively moves the sub-images corresponding to the individual radiation sources along the radial axis. Computer 28.3 would then compare the decoded amplitudes obtained from the default position of target image 52.3 to the decoded amplitudes obtained from the detuned position of target image 52.3 to determine the intensities of the distinct radiation sources. More preferably, patterns similar to FP3, FP4, F9 and F10 in modulator 22E of FIG. 8 are used to allow one to measure both the center wavelength and the total intensity of each encoded radiation component without detuning the position of target image 52.3.

Example 4

The fourth example of the dual-use analyzer 100 depicted in FIG. 1, analyzer 100.4, is a fluorescence imaging analyzer with the speed and sensitivity of a PMT. Radiation source 24.4 is an extended source comprised of the emission from a collection of different fluorescent samples. For example, the lanes of a multi-lane electrophoresis or the samples of a fluorescent labeled assay. Radiation emitted by source 24.4 is imaged by pre-encoder optic 36A.4 to form target image 52.4 (an extended image) substantially along a radial axis of modulator 22.4. Target image 52.4 is comprised of the sub-images of the collection of different fluorescent samples focused at substantially different points along said radial axis of modulator 22.4. Modulator 22.4 includes a number of radiation filters which encode the radiation emitted by the fluorescent samples to provide an encoded beam comprised of a plurality of encoded spatial components as modulator 22.4 is rotated about rotation axis 40. Preferably, target image 52.4 is aligned with the radiation filters such that the encoded components have a substantially one to one correspondence with the different fluorescent samples. The encoded beam is collected, directed and focused by post-encoder optic 36B.4 onto detector 26.4, a photo-multiplier tube (PMT), and the signals generated by the PMT in response to the encoded beam are analyzed by computer 28.4 to determine the amplitudes of the encoded components. Preferably, the spectral properties of the different fluorescent samples are measured by inserting a spectrometer or other wavelength filtering device between post-encoder optic 36B.4 and the PMT and scanning the wavelength of the radiation transmitted to the PMT. More preferably, a spectrograph or other wavelength separating device is used to direct a number of selected spectral components of the encoded beam to an equal number of PMTs. Most preferably, computer 28.4 would include a sufficient number of analog-to-digital converters (ADCs) such that the signals generated by the PMTs in response to the encoded beam could be analyzed substantially simultaneously. In this manner, the spectral properties of the collection of fluorescent samples can be measured substantially simultaneously with the speed and sensitivity of a PMT.

If necessary, analyzer 100.4 can be combined with the interlaced excitation mechanism of analyzer 300 (described in FIG. 10) to determine the excitation properties (e.g., the excitation spectrum) of the different fluorescent samples substantially simultaneously.

In reference to FIG. 9, for the analyzer described above, the position of the imaged fluorescence can be controlled by moving one or more optical elements to align target image 52.4 onto modulator 22.4. Preferably, source 24.4 includes a number of alignment spatial components (e.g., a number of known fluorescent species distributed at known spatial positions within 24.4) and modulator 22.4 includes a number of alignment channels to provide input to the alignment calibration algorithm 28.aca, which in turn, generates a control signal for hardware driver 28.drv to position one or more optical elements to align target image 52.4 onto modulator 22. More preferably, the alignment spatial components would also have known spectral emission properties for calibrating the wavelength filtering device or the wavelength separating device.

Example 5

The fifth example of the dual-use analyzer 100 depicted in FIG. 1, analyzer 100.5, is a spectrum analyzer which encodes both a dispersed image having a plurality of selected spectral components and an extended image comprised of the radiation transmitted through or reflected from one or more bandpass filters and/or dichroic beam splitters. This approach may be useful in situations where the radiation path through the analyzer may contain interfering gasses and vapors (or liquids) which can unpredictably effect the accuracy of the spectral measurements. In such instances it is preferable to minimize the optical path through the analyzer for those spectral components which are subject to the interference. Carbon dioxide ($CO_2$) is a well know case in point. Dispersive instruments used in applications where high transmission accuracy is required in the $CO_2$ spectral region typically require a nitrogen purge of the instruments uncontrolled path, i.e., the optical path not including the sample or sample cell. Analyzer 100.5 presents an alternative to this approach.

In Analyzer 100.5, the radiation source is a broad-band or multi-wavelength source having plurality of selected spectral components in two distinct spectral regions SR-I and SR-NI. SR-I contains those spectral components which are subject to the interference in the uncontrolled path. Preferably, analyzer 100.5 includes a dichroic mirror and one or more bandpass filters or a linear-variable filter (LVF) to filter the radiation in SR-I. Taken together, the radiation source, the dichroic mirror, and the collection of bandpass filters or LVF comprise sub-source 24.5.1, having a number of spatial components corresponding to the radiation transmitted through (or reflected from) the individual bandpass filters or positions along the LVF. The radiation in SR-NI, which is not subject to the interference, is designated sub-source 24.5.2. Pre-encoder optics, 36A.5 includes sub-optics, 36A.5.1 and 36A.5.2, for independently imaging 24.5.1 and 24.5.2, respectively, onto modulator 22.5. Sub-optic, 36A.5.1 forms a first target image 52.5.1, substantially along a first radial axis of modulator 22.5, and sub-optic 36A.5.2, which includes a diffractive or refractive element, forms a second target image 52.5.2, substantially along a second radial axis of modulator 22.5. Target image 52.5.1 is comprised of selected spectral components of 24.5.1 focused at substantially different points along the first radial axis of modulator 22.5. Target image 52.5.2, a dispersed image, is comprised of selected spectral components of 24.5.2 focused at substantially different points along the second radial axis of modulator 22.5. Modulator 22.5 has a number of radiation filters at different radii for encoding the radiation components of 24.5.1 and 24.5.2 to provide two encoded beams (EB1 and EB2, respectively) as modulator 22.5 is rotated about the rotation axis 40. Preferably, target image 52.5.1 is aligned with the radiation filters such that the encoded components of EB1 have a substantially one to one correspondence with the selected spectral components of 24.5.1. Preferably, target image 52.5.1 is aligned with the radiation filters such that the encoded components of EB2 have a substantially one to one correspondence with the selected spectral components of 24.5.2. Post-encoder optics, 36B.5 includes sub-optics, 36B.5.1 and 36B.5.2, for manipulating EB1 and EB2, respectively. EB1 is collected, directed and focused with 36B.5.1 onto a first detector 26.5.1, and EB2 is collected, directed and focused with 36B.5.2 onto a second detector 26.5.2. Preferably, computer 28.5 includes two ADCs for sampling the signals from detectors 26.5.1 and 26.5.2. Computer 28.5 then analyzes the signals generated by detector 26.5.1 and detector 26.5.2 in response to encoded beams, EB1 and EB2, respectively to determine the amplitudes of the encoded components in both spectral ranges. A sample or sample cell can be inserted between the source and the dichroic mirror for spectral analysis. Preferably, the total uncontrolled path for the spectral components of SR-I is made as small as possible to minimize the interference. In this manner, the spectral properties of a sample can be measured in the presence of interfering gasses or vapors.

Example 6

The sixth example of the dual-use analyzer 100 depicted in FIG. 1, analyzer 100.6, is compact spectrum analyzer which uses a collection of discrete radiation sources to provide a multi-spectral-component encoded source for analyzing a sample. Examples of discrete sources include laser diodes, light-emitting diodes or lamp/filter combinations. Preferably, radiation source 24.6 is comprised of a linear array of discrete sources. The radiation emitted by the array of sources is imaged to form target image 52.6 substantially along a radial axis of modulator 22.6. Preferably, the array of sources is positioned close to and along the radius of modulator 22.6 such that target image 52.6 is formed without needing pre-encoder optic 36A. Target image 52.6 is comprised of spatial components, the sub-images of the radiation emitted by the individual sources, which are focused (or centered) at substantially different points along said radial axis of modulator 22.6. Modulator 22.6 has a number of radiation filters at different radii for encoding the spatial components to provide an encoded beam as modulator 22.6 is rotated about the rotation axis 40. Preferably, the spatial components are aligned with the radiation filters such that the encoded components have a substantially one to one correspondence with the radiation emitted by the individual discrete sources. The encoded beam is collected, directed and focused with post-encoder optic 36B.6 onto detector 26. Computer 28 then analyzes the signal generated by detector 26 in response to the encoded beam to determine the amplitudes of the encoded components. A sample or sample cell can be inserted between the source 24.6 and detector 26. In this manner, the spectral properties of a sample can be measured.

In reference to FIG. 9, for analyzer 100.6 described above, the position of the array of discrete sources, and/or other optical elements, can be controlled by hardware driver 28.drv to align target image 52.6 onto modulator 22. Preferably, source 24.6 includes a number of alignment spatial components and modulator 22 includes a number of alignment channels to provide input to the alignment calibration algorithm 28.aca, which in turn, generates a control signal for hardware driver 28.drv to position one or more optical elements (e.g., a common structure onto which the array of discrete sources are mounted) to align target image 52.6 onto modulator 22.

Example 7

In some applications, it is necessary to measure the intensities of two or more groups of selected spectral components in two or more distinct spectral regions. For practical reasons, these spectral regions are often distinguished by the wavelength response characteristics of various radiation detectors. For example, a Mercury Cadmium Telluride (HgCdTe or MCT) responds to radiation roughly between 5 and 12 microns, a Lead Selenide (PbSe) detector responds to radiation roughly between 3 and 5 microns, an Indium Gallium Arsenide (InGaAs) detector responds to radiation roughly between 0.7 and 2.2 microns, and a photo-multiplier tube (PMT) responds to radiation roughly between 0.2 and 0.7 microns. In a given applications it may be necessary to measure selected spectral components in various combinations of these detector-specific spectral regions.

The seventh example of the dual-use analyzer 100 depicted in FIG. 1, analyzer 100.7, is a spectrum analyzer which uses a modulator 22.7 with one or more radiation filters which simultaneously encode selected spectral components in two distinct spectral regions. Radiation source 24.7 is comprised of selected spectral components in two distinct spectral regions, SR1 and SR2. Pre-encoder optic 36A.7 collects the radiation emitted by radiation source 24.7 and forms two target images, 52.7.1 and 52.7.2. Target image 52.7.1 is comprised of selected spectral components from SR1, and target image 52.7.2 is comprised of selected spectral components from SR2. The selected spectral components of 52.7.1 and 52.7.2 are focused at substantially different points along one or more radial axis of modulator 22.7. Modulator 22.7 has a number of radiation filters at different radii for encoding the spectral components to provide two encoded beams, EB1 and EB2, as modulator 22.7 is rotated about the rotation axis 40. Preferably, target images 52.7.1 and 52.7.2 are aligned with the radiation filters such that the encoded components have a substantially one to one correspondence with the selected spectral components of SR1 and SR2. More preferably, modulator 22.7 is an "array-like" pattern comprised of a large number of substantially orthogonal radiation filters substantially adjacent to one another, forming a substantially gapless encoding grid to simultaneously probe both spectral ranges of radiation source 24.7. Most preferably, the individual widths of the radiation filters in modulator 22.7 are engineered to provide encoded spectral components with constant wavelength bandwidth or constant energy bandwidth in a given spectral range. Using the "array-like" pattern of modulator 22.7, EB1 and EB2 contain substantially complete spectra in spectral ranges SR1 and SR2, respectively. Encoded beams EB1 and EB2 are collected and focused with post-encoder optic 36B.7 onto detectors 26.7.1 and 26.7.2, respectively. Preferably, detector 26.7.1 responds to the selected spectral components or SR1 and detector 26.7.2 responds to the selected spectral components or SR2. Preferably, computer 28.7 has two ADCs for sampling the signals from detectors 26.7.1 and 26.7.2. Computer 28 then analyzes the signal generated by the two detectors in response to the two encoded beams to determine the amplitudes of selected encoded components in the two spectral ranges substantially simultaneously. A sample or sample cell can be inserted between the source 24.7 and modulator 22.7. In this manner, the spectral properties of a sample in two distinct spectral ranges can be measured simultaneously.

The spectral regions cited in the example above where chosen for clarity and are not meant to limit the scope of the invention.

Example 8

The eighth example is based on analyzer 500 described above. Radiation source 524.8 is a eight-lane (or eight-capillary), four-dye-labeled electrophoresis responding to one or more components of excitation radiation. Radiation emitted or scattered by source 524.8 is imaged by pre-encoder optic 536A.8 to form target image 552.8 on modulator 522.8. Target image 552.8 is comprised of eight dispersed sub-images, corresponding to the eight excited electrophoresis lanes (or capillaries), with their respective dispersion axes substantially separated from one another (or carefully interlaced) along a common radius of modulator 522.8. Preferably, analyzer 500.8 includes a bandpass filter which transmits selected spectral components from each dispersed sub-image, while preventing the dispersed sub-images from interfering with one another. Modulator 522.8 includes eight sub-patterns for encoding the dispersed sub-images. Each sub-pattern includes a number of radiation filters to encode the selected spectral components as modulator 522.8 is rotated about rotation axis 540. Preferably, the selected spectral components are sufficient to determine the individual concentrations of the four dyes used in the electrophoresis. Preferably, target image 552.8 is aligned with modulator 522.8 such that the encoded components have a substantially one to one correspondence with the selected spectral components for each lane (or capillary). The encoded beam is collected, directed and focused with post-encoder optic 536B.8 onto detector 526.8, e.g., a photomultiplier tube (PMT). Computer 28 then analyzes the signal generated by detector 526.8 in response to the encoded beam to determine the amplitudes of the encoded components. Application-specific analytical function 28.asf then uses the decoded amplitudes to determine the individual concentrations of the four dyes in each of the lanes (or capillaries) as a function of time to generate eight four-color electropherograms.

If necessary, analyzer 500.8 can be combined with the interlaced excitation mechanism of analyzer 300 (described in FIG. 10) to determine the excitation properties (e.g., the excitation spectrum) of the different electrophoresis lanes (or capillaries). It is typical for each of the four dyes to have a unique excitation/response spectrum (or matrix). In this manner, the selected spectral components can be measured as a function of the excitation components substantially simultaneously to enhance the instruments specificity to the four dyes.

In reference to FIG. 9, for analyzer 500.8 described above, it is preferable that excitation radiation scattered from the individual lanes or capillaries be used as alignment components. Preferably, the bandpass filter attenuates the intensity of the alignment components such that the amplitude of the encoded alignment components are similar to the nominal encoded amplitudes of the selected spectral components. Preferably, each sub-pattern on modulator 522.8 would include one or more alignment filter pairs centered at the preferred or expected position of the alignment component(s) to provide input to the alignment calibration algorithm 528.aca. Preferably, alignment calibration algorithm 528.aca would compare the alignment signals to one or more calibration curves (generated as described above) to generate calibration coefficients which quantify the alignment error for each dispersed image in target image 552.8. Application-specific analytical function 528.asf would then use the calibration coefficients to compensate the encoded components for the alignment error. Most preferably, alignment calibration algorithm 528.aca would generate a control signal for hardware driver 528.drv to position one or more optical elements to properly align target image 552.8 onto modulator 522.8.

The number of excitation components, electrophoresis lanes (or capillaries), and the number of dyes was chosen for illustrative purposes, it being understood that arbitrary numbers of excitation components, electrophoresis lanes (or capillaries), and dyes are within the scope of the invention.

Statement of Scope

While the invention has been described above by reference to various embodiments, it will be understood that different combinations, changes and modifications may be made without departing from the scope of the invention which is to be defined only by the appended claims and their equivalents. Thus, instead of using the specific optical elements as described, including the specific placement of a sample cell in the beam path, other optical elements or optical systems may be used to collect, diffract, image and focus the radiation. For example, the pre-encoder optic 36a used in FIG. 1 to form a dispersed image, could be a focusing grating, a plane grating and focusing mirror or lens, a grating pair, a grating pair and a focusing mirror or lens, a prism and focusing mirror or lens, and the pre-encoder optic 36a used in FIG. 1 to form an extended image can include a simple focusing mirror or lens, a camera lens system, an interferometer, or a focusing mirror or lens and collection of bandpass filters or a linear variable filter. In addition, various light pipes, waveguides and optical fibers (and collections thereof) can be used to bring the input radiation from or direct the encoded signal to a number of remote sampling stations.

Where the modulator 22 of FIG. 1A and the modulators of the various other embodiments in the other figures are designed to be rotated about axis 40 to encode corresponding radiation components, the filters on the modulators occupy annular regions of the disk as shown in the various figures of this application. This invention, however, is not limited to such implementation. Instead of annular regions, the filters, such as filters 50a, 50d may form four linear rows on the surface of the modulator, and the modulator may be reciprocated linearly along a direction substantially parallel to the rows of filters. The target image 52 is then projected in a direction with its length transverse (preferably perpendicular) to the direction of the rows of filters so that the image overlaps preferably all four rows of the filters. Such and other variations are within the scope of the invention.

The numerous embodiments of the invention should be considered as design strategies which can be used in various combinations to facilitate a given spectroscopy or imaging application. In particular, modulator patterns comprised of various combinations of radiation filters and filter pairs shown in this document are within the scope of the invention.

What is claimed is:

1. A radiation spectrum analyzer comprising:
   at least one source providing radiation having at least two selected radiation components;
   first optics focusing said radiation components at substantially different points along an encoding axis in an encoding plane; a two dimensional spatial radiation modulator rotated about a rotation axis and positioned in said encoding plane so that said encoding axis is substantially along a radial axis, said modulator having at least two radiation filters at different radii from said rotation axis for modulating the intensities of said components to provide an encoded beam as said modulator is rotated about said rotation axis;
   wherein said first optics includes at least one obscuration to selectively block radiation from one or more of said radiation filters;
   a detector;

second optics collecting and directing said encoded beam onto said detector, causing the detector to provide an output; and computer analyzing signals generated by said detector in response to said encoded beam.

2. The analyzer of claim 1, wherein said obscuration is movable.

3. The analyzer of claim 2, wherein said obscuration is translated along said radial axis.

4. A radiation spectrum analyzer comprising:

two or more different radiation detectors, each said radiation detector responding to radiation in a substantially distinct spectral region of two or more distinct spectral regions;

at least one source providing radiation having at least one selected radiation component in each of said two or more distinct spectral regions;

first optics focusing said radiation component(s) in a first spectral region of said two or more distinct spectral regions at substantially different points along a first encoding axis in an encoding plane, said first optics collecting and focusing said radiation components in a second spectral region of said two or more distinct spectral regions at substantially different points along a second encoding axis in said encoding plane;

a two dimensional spatial radiation modulator rotated about a rotation axis and positioned in said encoding plane so that said two or more encoding axes are substantially along at least one radial axis, said modulator having a plurality of radiation filters at different radii from said rotation axis for modulating the intensities of said components thereby encoding the components to provide two or more encoded beams as said modulator is rotated about said rotation axis, each of said encoded beams containing one corresponding encoded component of said encoded components in said two or more distinct spectral regions;

second optics collecting and directing each of said encoded beams onto a corresponding detector of two or more detectors, causing each said detector to provide an output; and;

computer analyzing signals generated by said detectors in response to said encoded beams.

5. The analyzer of claim 4, wherein one of said two or more distinct spectral regions is substantially defined by the wavelength response of an Indium Gallium Arsenide radiation detector.

6. The analyzer of claim 4, wherein one of said two or more distinct spectral regions is substantially defined by the wavelength response of a Mercury Cadmium Telluride radiation detector.

7. The analyzer of claim 4, wherein one of said two or more distinct spectral regions is substantially defined by the wavelength response of a Lead Selenide radiation detector.

8. The analyzer of claim 4, wherein one of said two or more distinct spectral regions is substantially defined by the wavelength response of a Photo-multiplier tube radiation detector.

9. The analyzer of claim 4, wherein said radiation filters reflect radiation.

10. A radiation spectrum analyzer comprising:

a source comprising radiation from two or more distinct samples;

first optics collecting, dispersing and focusing said radiation from two or more distinct samples to form two or more corresponding dispersed images, said images dispersed by wavelength along two or more corresponding dispersion axes onto a plane, each said dispersed image having a plurality of selected spectral components;

a two dimensional spatial radiation modulator rotated about a rotation axis and positioned in said plane so that said dispersion axes are substantially along at least one radial axis, said modulator having a plurality of radiation filters at different radii from said rotation axis, each said filter modulating the intensity of a corresponding selected spectral component in at least one of said dispersed images to provide two or more encoded beams, each of said two or more encoded beams corresponding to one of said two or more dispersed images, each said encoded beam comprising at least one encoded component from a corresponding dispersed image, wherein the amplitudes of said encoded components change as said modulator is rotated about said rotation axis;

at least one detector;

second optics collecting and directing said encoded beams onto said at least one detector, causing said at least one detector to provide an output; and computer analyzing signals generated by each said detector in response to said encoded beam.

11. A two dimensional spatial radiation modulator adapted to be rotated about a rotation axis to modulate at least one component of an incident radiation beam to encode said beam, said modulator comprising a substrate and at least one radiation filter located at a radius from said rotation axis, said filter comprising an annular region substantially encompassing a first number of non-contiguous regions having optical characteristics substantially different from said substrate, said non-contiguous regions being patterned substantially within said annular region to modulate the intensity of a corresponding radiation component as a halftone representation of a substantially smooth function having a second number of local maxima as said modulator is rotated one revolution about said rotation axis, wherein said first number of non-contiguous regions is greater than said second number of local maxima.

12. The modulator of claim 11, wherein said non-contiguous regions comprise regions that are non-contiguous along at least a radial direction and a non-radial direction pattern is engineered to increase the number of available levels of contrast in said halftone representation.

13. The modulator of claim 11, wherein said pattern is engineered to control the modulation depth of said corresponding radiation component.

* * * * *